United States Patent [19]
Brown et al.

[11] Patent Number: 5,303,575
[45] Date of Patent: Apr. 19, 1994

[54] APPARATUS AND METHOD FOR CONDUCTING AN UNSUPERVISED BLOOD ALCOHOL CONTENT LEVEL TEST

[75] Inventors: Gordon R. Brown, Toronto; Gerald H. Herlinger, Bolton, both of Canada

[73] Assignee: Alcotech Research Inc., Mississauga, Canada

[21] Appl. No.: 69,862

[22] Filed: Jun. 1, 1993

[51] Int. Cl.$^5$ .................................. G01N 33/497
[52] U.S. Cl. .................................. 73/23.3; 364/497; 422/84; 436/900
[58] Field of Search .................. 73/23.3; 340/576; 128/719; 422/84; 436/900; 364/497, 499, 413.02, 413.03, 413.08, 413.09

[56] References Cited

U.S. PATENT DOCUMENTS

| | | | |
|---|---|---|---|
| 3,338,087 | 8/1967 | Moberg et al. | 73/23.3 |
| 3,764,270 | 10/1973 | Collier et al. | 73/23.3 X |
| 3,858,434 | 1/1975 | Hoppesch et al. | 73/23.3 |
| 3,877,291 | 4/1975 | Hoppesch et al. | 73/23.3 |
| 4,093,945 | 6/1978 | Collier et al. | 340/576 X |
| 4,132,109 | 1/1979 | Vandersyde | 73/23.3 |
| 4,300,384 | 11/1981 | Wiesner et al. | 73/23.3 |
| 4,592,443 | 6/1986 | Simon | 73/23.3 X |
| 4,749,553 | 6/1988 | Lopez et al. | 422/84 |
| 4,868,545 | 9/1989 | Jones | 73/23.3 X |
| 4,926,164 | 5/1990 | Porter et al. | 340/576 |

Primary Examiner—Hezron E. Williams
Assistant Examiner—Joseph W. Roskos
Attorney, Agent, or Firm—Patrick J. Hofbauer

[57] ABSTRACT

An automated unsupervised apparatus for conducting a blood alcohol content level test on an individual user, and subsequently discerning and displaying a meaningful test result, is disclosed. The apparatus comprises an alphanumeric display for instructing the individual user to blow into the apparatus so as to provide a breath sample. A pressure switch is used to monitor the gauge pressure of the individual user's breath sample in order to determine whether the gauge pressure is at or above a threshold value for a predetermined length of time, typically three seconds. The alphanumeric display instructs the individual user to wait and blow again in the event that the gauge pressure does not remain at or above the threshold value for the predetermined length of time. A testing sample of the individual user's breath sample is captured in a fuel cell type alcohol concentration sensor. The alcohol concentration sensor in conjunction with an operational amplifier, a peak circuit detector and an analogue to digital convertor, effects an automated electrochemical analysis of the testing sample. A measurement value of the alcohol content of the testing sample is produced, and introduced into a microprocessor, where a numeric value derived from the measurement value and related to the individual user's blood alcohol content level, is calculated. The alphanumeric display displays this numeric value and the category corresponding to the numeric value as being one of "pass", "warn", and "fail".

29 Claims, 11 Drawing Sheets

APPARATUS AND METHOD FOR CONDUCTING AN UNSUPERVISED BLOOD ALCOHOL CONTENT LEVEL TEST

FIELD OF THE INVENTION

This invention relates to electronic based devices for automatically conducting an unsupervised chemical analysis test and more particularly to electronic based devices for testing the blood alcohol content of an individual user and meaningfully displaying the results of such a test. Further, this invention relates to the method of conducting such unsupervised chemical analysis tests, used in conjunction with such devices.

BACKGROUND OF THE INVENTION

Operating a motor vehicle while under the influence of alcohol, or at least being in the situation of wanting to operate a motor vehicle while under the influence of alcohol, is a widespread problem in modern society. While some individual users are not generally concerned about operating a motor vehicle while under the influence of alcohol, others are genuinely concerned about doing so because of the potential adverse consequences. It is sometimes difficult for an individual user to be able to objectively judge whether they have exceeded the threshold for o being able to legally operate a motor vehicle, particularly as objective judgment is impaired as alcohol is consumed. A very common threshold value of blood alcohol content level for determining whether an individual user is able to legally operate a motor vehicle is 80 milligrams of alcohol per liter of blood, or otherwise expressed, 0.08% blood alcohol content.

In order to make it possible for an individual user who has been consuming alcohol to make a proper and objective judgment as to whether he might be in a condition to legally operate a motor vehicle, it is necessary to test for that individual user's blood alcohol content in some manner. While it is possible to directly test an individual user's blood alcohol content level by way of taking a blood sample and analyzing that sample, this method is generally unsatisfactory for self-administration and may raise legal issues when administered by others since it involves the invasion of an individual user's body by a needle. It is also possible to relatively accurately discern an individual user's blood alcohol content level in an indirect manner, by analyzing a sample of an individual user's breath that has been obtained from the bottom portion of the individual user's lungs, which sample is hereinafter referred to as a testing sample. Many establishments that serve alcohol have testing devices located within their premises that allow an individual user to attempt to discern his or her blood alcohol content level in this manner.

Various types of such testing devices utilizing different operating mechanisms are known. Each type, however, receives an individual user's breath sample and ultimately produces by way of an electrochemical reaction, an electrical output signal that is representative of the blood alcohol content level of the individual user. Various means are then used in the testing devices to convert the electrical output signal from the electrochemical operating mechanisms to an output that is properly representative of the blood alcohol content level of the individual user being tested. This output might be the actual numeric value of the individual user's blood alcohol content level or might be, for example, a categorization of that level, as either "pass", "warn", or "fail".

As mentioned previously, in order to receive a reliable representative testing sample from an individual user's breath sample, it is necessary to obtain the testing sample from the air at the bottom of the individual user's lungs. Accordingly, in order to provide such a testing sample, the individual user must (1) wait until the testing device is ready, (2) take a deep breath, (3) blow (exhale) at a certain threshold rate, which can be measured as a gas pressure, and (4) maintain at least this threshold gas pressure for a predetermined length of time (generally considered to be at least three seconds). The testing sample should not be taken until after this predetermined length of time has expired, but does not need to last for more than about one half second thereafter. Presently available self-administered breath testing devices do not make provision for informing an individual user of the proper procedure for providing a testing sample. It has been found that presently available self-administered breath testing devices generally lack a sufficient and proper operating methodology necessary for permitting the easy and proper use by an untrained individual user in an unsupervised setting.

Further, an individual user must know how to correctly interpret the results that are displayed, and also how to use these results in a safe and appropriate manner. An individual user should know what the legal limit of alcohol is, must be informed of whether he or she is over this legal limit, should be informed if he or she is only slightly below the legal limit, and should be advised to perform a retest in certain situations, such as when he or she is only slightly below the legal limit, as it is extremely important in this situation to determine whether an individual user's blood alcohol content is rising or falling. The individual user should also be advised if the measured alcohol content is extremely high, and that such a high reading might also indicate that the test has not been performed properly.

It has been found that presently available prior art self-administrable breath testing devices generally lack a sufficient and proper operating methodology necessary to provide such information in its entirety, in a sufficiently useful manner.

One example of a prior art device can be found in Canadian Patent No. 997,585 to Hoppesch et al., which patent discloses a breath tester for supervised use. The breath tester disclosed therein has an analog meter that indicates the alcohol level from an individual user's breath, and also has three light emitting diodes that signal "pass", "warn", or "fail". In order to use this device, it is necessary to know that the analog meter must be in a near 0 condition at the start of the test, which indicates that the detector unit has been sufficiently purged of alcohol and is providing a null electrical output. Further, this device does not indicate when to blow, how long to blow, nor does it test for how hard the individual user is blowing, nor does it inform the individual user if he or she is not blowing hard enough. Further, no instructions as to retesting are provided, in the event that the individual user's blood alcohol content level is near the legal threshold, in order to help the individual user determine whether his or her blood alcohol content level is rising or falling. The unit does, however, indicate when an individual user must wait to use it and when it is ready to be used, and also when it is in its testing mode. It is not possible to properly use this device without specific knowledge of how to use the device, which would be gained by either previous experience or specific instruction. Accordingly, it is not suitable for unsupervised use by an untrained individual user.

U.S. Pat. No. 4,093,945 to Collier et al. discloses a breath testing system suitable for direct installation in an automobile. This system indicates when it is ready to be used, when it is actually testing, and whether the results of the test are pass or fail. These indications are all presented by way of small lights or light emitting diodes. This system has all of the shortcomings of the prior art device described above, except that it can be used in an unsupervised manner. This is because an individual user would need to instruct himself in the proper operation of this device if it was installed in an individual user's car, failing which the car would be rendered inoperable. Such would not be the case with a device installed in a licensed drinking establishment.

One desirable aspect of testing for an individual user's blood alcohol content level is to re-test an individual user whose first test indicates that he/she is near the maximum legal blood alcohol content level, but not over it. If only one test is performed, it is not known whether that individual user's blood alcohol content level is rising or falling. The desirability of this feature is shown in U.S. Pat. No. 4,926,164 to Porter et al., wherein a vehicle breath monitoring device is adapted to require a retest after 8 minutes if a blood alcohol content level slightly below the legal limit is realized upon a first test. The device only beeps after the 8 minute period in order to indicate that a retest should be done. Again, specific knowledge of the operation of the device must be had by an individual user using the device in order to use it properly.

It is also known to provide an electronic digital display of the blood alcohol level, as taught in U.S. Pat. No. 4,749,553 to Lopez et al. This patent also teaches the use of digital electronics to perform the testing operation and also to store the results of the test in random access computer memory for later use. It does not however, provide adequate instructions for the proper operation of the device.

Another important aspect of properly and accurately testing for blood alcohol content level by way of capturing and analyzing an individual user's breath sample, is informing that individual user that the test results might be inaccurate if the test results are very high, which high test results may be caused by the presents of alcohol in the individual user's mouth. It is necessary to inform the individual user that the test should be performed again after the individual user's mouth has been rinsed. Such instructions are not provided by the various devices disclosed in the prior art.

It has been found that it is common for individual users to not test for their blood alcohol content level upon leaving a licensed drinking establishment, even though the individual users might be unsure of whether their blood alcohol content level is within a threshold range for legally operating a motor vehicle. In many cases, the deficiencies of prior art blood alcohol content level testing devices installed in these drinking establishments do not provide adequate enough information on the use of the device, nor do they provide full and complete information about the test results, assistance on how to correctly interpret the test results and how to use the test results in a safe and appropriate manner.

It is an object of the present invention to provide an apparatus for conducting an unsupervised test of the level of blood alcohol content of an individual user, which apparatus allows that individual user to accurately and objectively determine his/her blood alcohol content level.

It is another object of the present invention to provide an apparatus for conducting an unsupervised test of the level of blood alcohol content of an individual user, which apparatus makes provisions for informing that individual user on an interactive basis about the proper procedures for providing a testing sample.

It is yet another object of the present invention to provide an apparatus for conducting an unsupervised test of the level of blood alcohol content of an individual user, which apparatus provides instructions to permit the easy and proper use thereof by an untrained individual user in an unsupervised setting.

It is a further object of the present invention to provide an apparatus for conducting an unsupervised test of the level of blood alcohol content of an individual user, which apparatus informs the individual user how to correctly interpret the test results.

It is yet a further object of the present invention to provide an apparatus for conducting an unsupervised test of the level of blood alcohol content of an individual user, which apparatus informs the individual user in the event that the test has not been performed properly.

It another object of the present invention to provide an automated method for conducting an unsupervised test of the level of blood alcohol content of an individual user, which method allows that individual user to accurately and objectively determine his/her blood alcohol content level.

It is a further object of the present invention to provide an automated method for conducting an unsupervised test of the level of blood alcohol content of an individual user, which method makes provisions for informing that individual user on an interactive basis about the proper procedures for providing a testing sample.

It is yet a further object of the present invention to provide an automated method for conducting an unsupervised test of the level of blood alcohol content of an individual user, which method provides instructions to permit the easy and proper use thereof by an untrained individual user in an unsupervised setting.

It is yet a further object of the present invention to provide an automated method for conducting an unsupervised test of the level of blood alcohol content of an individual user, which method informs the individual user how to correctly interpret the test results.

It is yet a further object of the present invention to provide an automated method for conducting an unsupervised test of the level of blood alcohol content of an individual user, which method informs the individual user in the event that the test has not been performed properly.

SUMMARY OF THE INVENTION

In accordance with one aspect of the present invention, there is also provided an automated unsupervised apparatus for conducting a blood alcohol content level test on an individual user, and subsequently discerning and displaying a meaningful test result. The apparatus comprises:

alphanumeric display means for instructing the individual user to commence blowing into the apparatus so as to provide a breath sample;

pressure switch means for monitoring the gauge pressure of the individual user's breath sample in order to determine whether the gauge pressure is at or above a threshold value gauge pressure;

timer means for determining whether the gauge pressure of the individual user's breath sample remains at or above the threshold value gauge pressure for a predetermined length of time;

alphanumeric display means for instructing the individual user to wait and blow again in the event that the gauge pressure does not remain at or above the threshold value for the predetermined length of time;

means for capturing a testing sample that is a representative portion of the individual user's breath sample subsequent to the individual user providing a breath sample at or above the threshold value for the predetermined length of time;

means for effecting an automated electrochemical analysis of the testing sample;

means for producing a measurement value of the alcohol content of the testing sample; and microprocessor means for calculating a numeric value derived from the measurement value, the numeric value thereby being related to the individual user's blood alcohol content level;

wherein said alphanumeric display means also displays to the individual user one of either (1) the category corresponding to the numeric value as being one of "pass", "warn", and "fail" and (2) the numeric value derived from the measurement value.

In accordance with another aspect of the present invention, there is provided an automated method of conducting a blood alcohol content level test on an individual user through the use of an unsupervised apparatus, and subsequently discerning and displaying a meaningful test result. The method comprises the steps of:

(a) (i) instructing the individual user by way of an alphanumeric display means to commence blowing into the apparatus so as to provide a breath sample;

(b) monitoring the gauge pressure of the individual user's breath sample in order to determine whether the gauge pressure is at or above a threshold value gauge pressure;

(c) determining whether the gauge pressure of the individual user's breath sample remains at or above the threshold value gauge pressure for a predetermined length of time;

(d) instructing the individual user by way of an alphanumeric display means to wait and blow again in the event that the gauge pressure does not remain at or above the threshold value for the predetermined length of time;

(e) performing steps (c) and (d) until the individual user provides a breath sample at or above the threshold value for the predetermined length of time;

(f) capturing a testing sample that is a representative portion of the individual user's breath sample subsequent to the individual user providing a breath sample at or above the threshold value for the predetermined length of time;

(g) effecting an automated electrochemical analysis of the breath sample so as to produce a measurement value of the alcohol content of the representative portion of the individual user's breath sample;

(h) obtaining the measurement value resulting from the automated electrochemical analysis;

(i) calculating a numeric value derived from the measurement value, the numeric value thereby being related to the individual user's blood alcohol content level; and, (j) (i) displaying to the individual user by way of an alphanumeric display means, one of either (1) the category corresponding to the numeric value as being one of "pass", "warn", and "fail" and (2) the numeric value derived from the measurement value.

Other objects, features and characteristics of the present invention, as well as methods of operation and functions of the related elements of the structure, and the combination of parts and economies of manufacture, will become more apparent upon consideration of the following detailed description and the appended claims with reference to the accompanying drawings, all of which form a part of this specification.

DETAILED DESCRIPTION OF A PREFERRED EMBODIMENT

Introduction to the Drawings

Figure 1A:
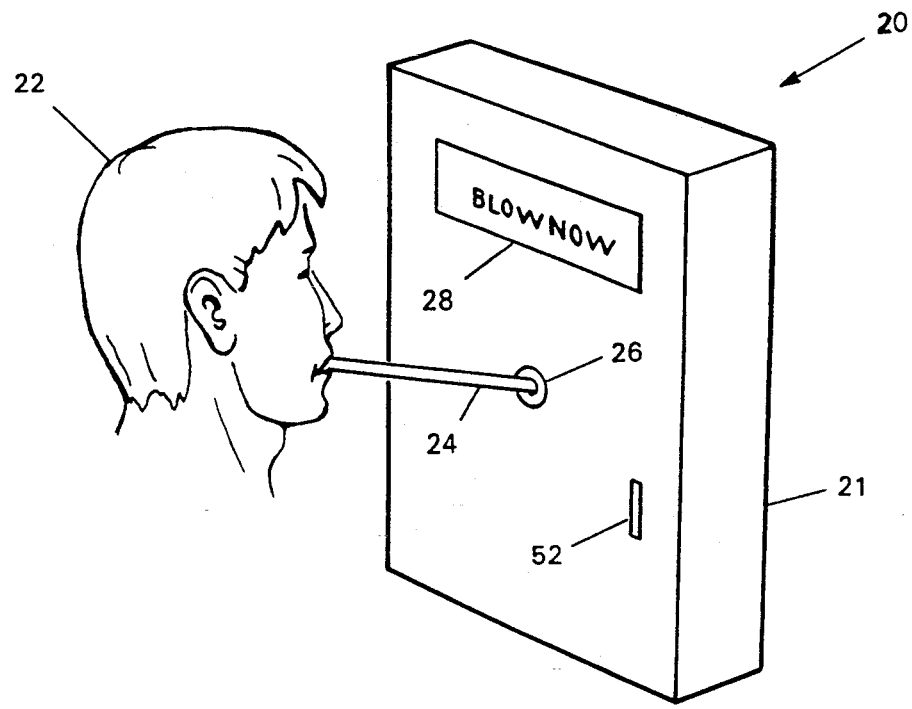
FIG. 1A is a perspective view of a preferred embodiment of a breath testing apparatus according to the present invention in situ, with a user about to blow through a straw into the breath testing unit so as to provide a breath sample.
Figure 1B:
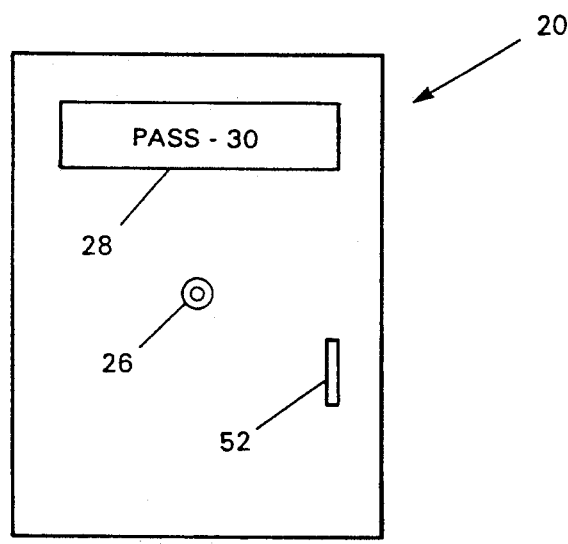
FIG. 1B is a front elevational view of the breath testing device of FIG. 1A displaying the results of the analysis of the test performed on the breath sample of the individual user shown in FIG. 1A.

Reference will now be made to FIGS. 1A and 1B, which show a preferred embodiment of breath testing apparatus according to the present invention, as indicated by the general reference numeral 20, in use. The breath testing apparatus 20 comprises a robust cabinet 21 that is adapted to withstand potential abuse that might be received from an intoxicated person who has been informed by the apparatus that he is over the legal blood alcohol limit for driving. Further, the components of the apparatus 20, including the computer circuitry, are of very high quality, so as to minimize the chance of malfunction of the breath testing apparatus 20, and also to reduce the amount of maintenance required.

In FIG. 1A, an individual user 22 is using the breath testing apparatus 20 to analyze his blood alcohol content level. The individual user 22 has placed a straw 24 into the input 26 of the breath testing apparatus 20 and is about to blow through the straw 24 in order to provide a breath sample. A testing sample is ultimately obtained from this breath sample, as will be described subsequently.

An alphanumeric display means 28 on the breath testing apparatus 20, displays various instructions, messages and the results of each blood alcohol content level test that is performed. As shown, the display means 28 is a sixteen character alphanumeric display; preferably either a conventional liquid crystal display or a light emitting diode display. At this point in the test, the alphanumeric display means 28 is displaying an instruction to the individual user 22 that reads "BLOW NOW", which instruction is one of a series of complete step-by-step instructions that guide the individual user 22 through the steps that define the method of the present invention. When the individual user 22 starts to blow, another alphanumeric message will be displayed to further instruct such user 22, subsequently, with several messages displayed in proper sequence to completely instruct the individual user 22 on the proper use of the breath testing device 20 of the present invention. Further, subsequent results and interpretation of these results are displayed, as shown in FIG. 1B. In FIG. 1B, the individual user 22 performing the test has completed the portion of the test where a breath sample is provided. As shown on the display means 28, the individual user 22 has a blood alcohol content level of about 30 mg./100 ml of blood, which is well below the normally recognized legal limit of 80 mg./ml of blood. The alphanumeric display means 28 correspondingly displays the results of the test in the form "PASS - 30".

Figure 2:
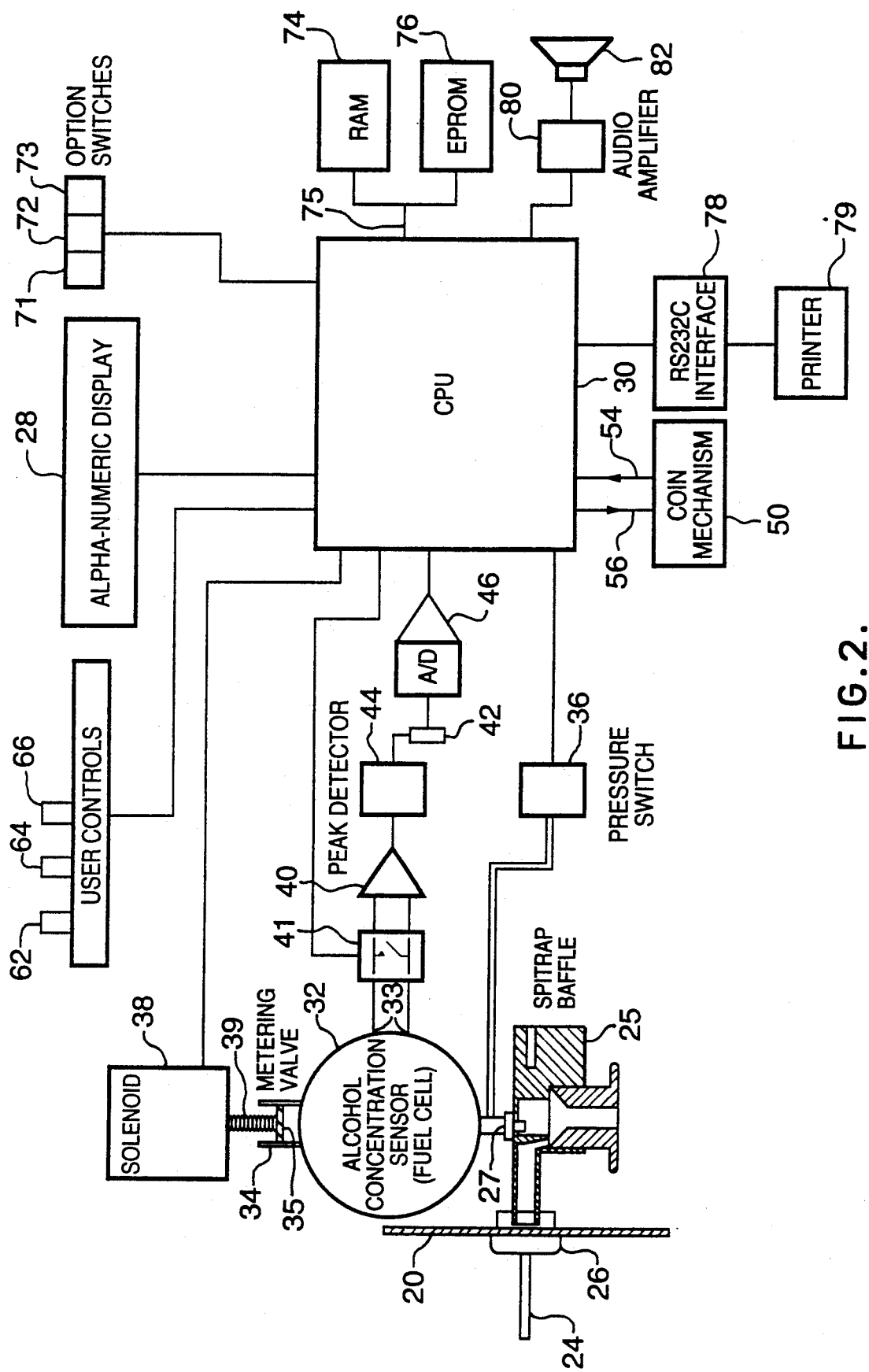
FIG. 2 is a pictorial schematic view of the components of the apparatus of the present invention illustrating how they are functionally interconnected.

Reference will now be made to FIG. 2, which shows the components of the breath testing apparatus 20, and the functional interconnection of these components. The overall operation of the apparatus 20 is controlled by a CPU 30, which is preferably a standard Motorola 6803 CPU, or may be any other standard suitable CPU. Indirectly connected to and controlled by the CPU 30, (as more fully described below), is an alcohol concentration sensor 32, which is adapted to effect automated electrochemical analysis of the testing sample of the individual user's 22 breath sample. Preferably, the alcohol concentration sensor 32 is in the form of a fuel cell. A suitable fuel cell is manufactured by and available from Lion Laboratories Limited of Barry, United Kingdom, and is in common use throughout the world in various breath monitoring systems. This fuel cell and its operatively related co-operating components are fully described in the LION ALCOLMETER SL-2 TECHNICAL SERVICE MANUAL, published by Lion Laboratories Limited which document is hereby incorporated by reference.

The alcohol concentration sensor 32 is connected in fluid communication to a feed tube 27, which is in turn connected in fluid communication, to a spitrap baffle 25. The spitrap baffle 25 is connected at its input end to the input 26 of the apparatus 20 so as to be in fluid communication with the straw 24, which is used by the individual user 22 to provide a breath sample. A portion of the breath sample is directed into the feed tube 27, which is in fluid communication with the alcohol concentration sensor 32. The feed tube 27 is also in fluid communication with a pressure switch 36 by way of an auxiliary tube 37. An increase in the pressure in the feed tube 27 causes a corresponding increase in pressure at the input of the pressure switch 36. The pressure switch 36 becomes electrically closed when the air pressure at its input reaches a threshold value gauge pressure. When the pressure switch is electrically closed, a circuit in the CPU 30 is completed so as to signal the closure of the pressure switch 36. The resultant action of the CPU 30 will be discussed subsequently.

The alcohol concentration sensor 32 has a metering valve 34 mechanically operatively connected thereto. The metering valve 34 controls the flow of fluid (i.e., a testing sample) into the alcohol concentration sensor 32. The metering valve 34 has a "set" button 35 that is depressed during the time when a testing sample is not required and released when a testing sample is required. A solenoid controlled activating mechanism 38 is spring biased by a biasing spring 39 to depress the "set" button 35 when a testing sample is not required, which is most of the time. When a testing sample is required, the solenoid controlled activating mechanism 38 pulls back against the biasing spring 39, thereby releasing the "set" button 35 of the alcohol concentration sensor and causing a testing sample of about 1.5 cc. to be captured by the alcohol concentration sensor. The solenoid controlled activating mechanism 38 is activated by the CPU 30 in conjunction with the pressure switch 36 becoming electrically closed.

The electrical output 33 of the alcohol concentration sensor 32, which provides a direct current analogue signal proportional to the alcohol concentration of the sample that has been drawn thereinto, is connected in electrically conductive relation to an operational amplifier 40. The operational amplifier 40 amplifies the signal from the output 33 of the alcohol concentration sensor 32 so as to be at a suitable level for input to a peak detector circuit 44.

Figure 8:
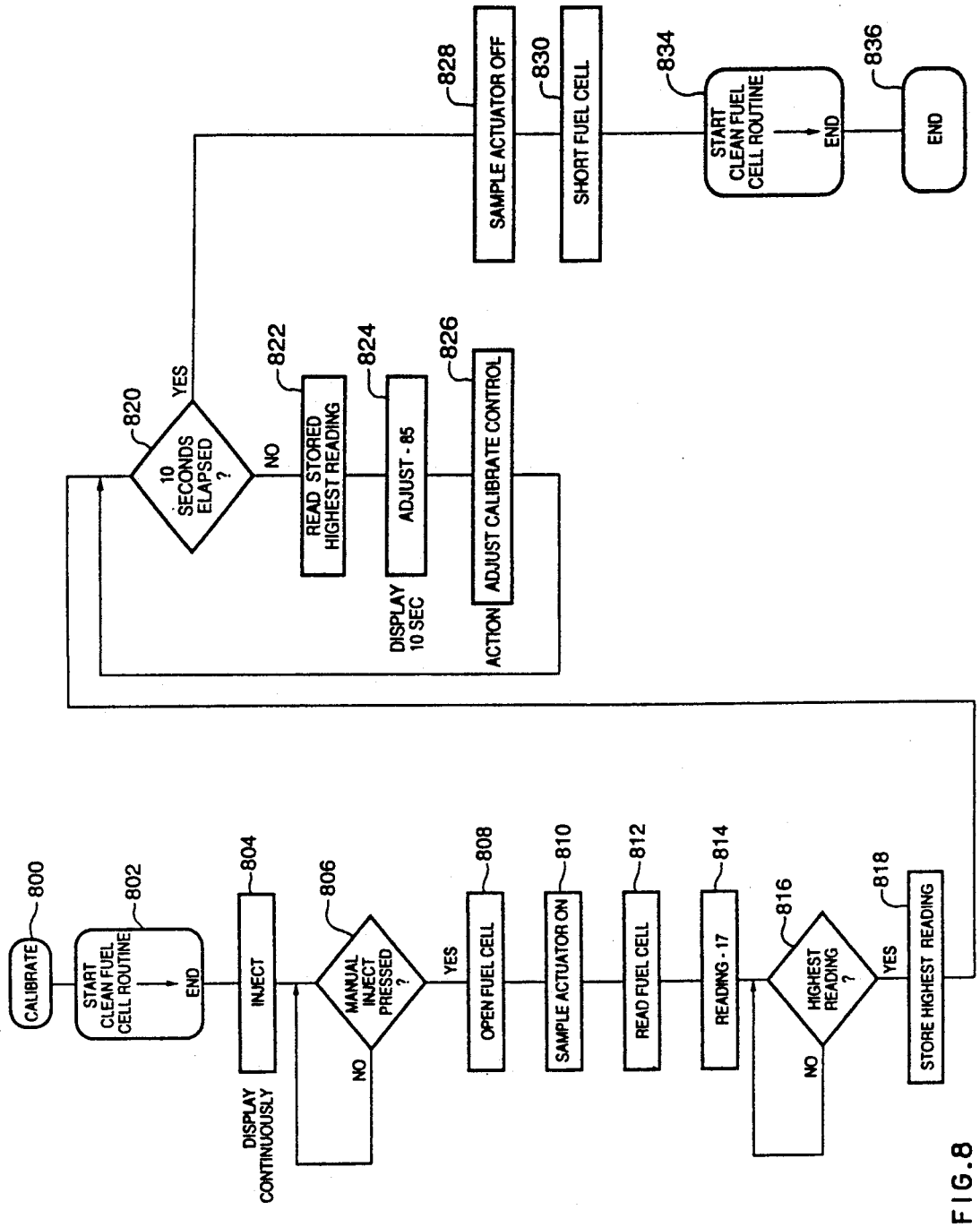
FIG. 8 is flow chart showing the calibrate routine of the method of the present invention.

The peak detector circuit 44 receives the analogue voltage from the operational amplifier 40. A potentiometer 42 is connected from the output of the peak detector circuit 44 to the input of the A/D converter 46 to allow the signal level to be adjusted, as will be described subsequently with reference to the CALIBRATION routine, as shown in FIG. 8. The peak detector circuit 44 is adapted to monitor this voltage and to produce a output voltage corresponding to the peak voltage received from the operational amplifier 40. This output voltage is a measurement value of the alcohol content of the testing sample that is the representative portion of the individual user's 22 breath sample. When this peak voltage is realized, the peak detector circuit 44 passes this peak voltage to its output 45. In this manner, the alcohol concentration sensor 32, the operational amplifier 40 and the peak detector circuit 44 are the means for effecting an automated electrochemical analysis of the breath sample provided by the individual user 22.

The output 45 of the peak detector circuit 44 is electrically connected to an analogue to digital (A/D) converter 46. The peak voltage obtained from the operational amplifier 40, as determined by the peak detector circuit 44, is passed to the analogue to digital (A/D) converter 46, which converts this peak voltage to an 8-bit digital value that is a numeric value derived from the measurement value of the alcohol content of the testing sample of individual user's 22 breath sample. This numeric value is then passed into the CPU 30, where it is used as will be described subsequently. This 8-bit digital value is representative of the alcohol concentration in the individual user's 22 breath sample and is therefore also representative of the blood alcohol content of the individual user 22.

Also electrically connected to the alcohol concentration sensor 32 is a shorting relay 41, which is also controlled by the CPU 30. The shorting relay 41 operates in conjunction with the solenoid controlled activating mechanism 38 as previously mentioned. When a testing sample is not required, the shorting relay 41 is in its resting state, such that the shorting relay 41 shorts out the output 33 of the alcohol concentration sensor 32 so as to preclude a build-up of electrical potential across its output 33. When a testing sample is required, it is necessary to: 1) remove the short circuit across the output 33 of the alcohol concentration sensor 32 by activating the shorting relay 41; and, concurrently, 2) release the "set" button 35, which release causes a testing sample to be drawn into the alcohol concentration sensor 32. Resultingly, the electrical potential that is caused by the subsequent reaction of the alcohol molecules in the testing sample, is allowed to build up at the output 33 of the alcohol concentration sensor. After the peak electrical potential value is realized, and ultimately captured by the peak detector circuit 44, the shorting relay 41 is deactivated, so as to again short out the output 33 of the alcohol concentration sensor 32, concurrent with the depression of the "set" button 35.

A conventional coin mechanism 50, which accepts coins through its coin input 52 is electrically connected to the CPU 30 by way of an output line 54 and an input line 56. When a coin is inserted through the coin input 52, the coin mechanism 50 signals the CPU 30 by way of its output line 54. The coin mechanism 50 is controlled by the CPU 30 by way of its input line 56 such that coins may be accepted only at certain times, as designated by the CPU 30.

A number of user controls, which are preferably push-buttons, are also mounted on the main circuit board. In the preferred embodiment, there is a calibrate button 62, a show meter button 64, and a manual inject button 66. These push-buttons are electrically connected to appropriate inputs of the CPU 30. The calibrate button 62 is used to invoke the calibrate routine, for calibrating the breath testing apparatus 20. The show meter button 64 is used to invoke the coin meter routine, which displays the number of tests that have been conducted and other information related thereto. The show meter button 64 is also used to start a printer 79 printing when the PRINTER routine is in operation. The manual inject button 6 is used in order to allow the portion of the routine being processed by the CPU that requires a person to provide a proper breath sample, to be skipped. Skipping of this portion of the routine allows for calibration to be performed, as will be described subsequently, with reference to FIG. 8, and also allows for the breath testing apparatus 20 to be demonstrated or tested by using a suitable aerosol spray can that delivers a gas having a known alcohol concentration.

A number of option switches that are used to control the operation of the apparatus 20, are also mounted on the main board. A free test option switch 71 is used to put the apparatus into a "free test" mode, which allows tests to be performed for free, and which will be described subsequently with reference to FIG. 4. A coins required option switch 72 is used to select the required number of coins that must be entered in order to start the normal operating routine of the breath testing apparatus 20, thereby allowing the price of using the apparatus 20 to be selectable. A format option switch 73 allows the apparatus 20 to be switched between Canadian and U.S. formats in the preferred embodiment, or other formats as necessary, which controls some information and perimeters that are subsequently displayed. The option switches 71, 72, 73 are preferably standard dip switches, which are commonly used in the industry for such purposes. The function and operation of the option switches 71, 72, 73 will be described in greater detail subsequently.

In the preferred embodiment, 2 kilobytes of computer memory in the form of non-volatile random access memory (RAM) 74 are connected in electrically conductive relation, by way of a common computer bus 75, with the CPU 30. This random access memory (RAM) 74 is used to store data regarding test results produced by the breath testing apparatus 20, such as the number of tests performed, the aggregate of the numeric values calculated, the number of numeric values in each of the categories "PASS", "WARN", and "FAIL", and the amount of money input into said apparatus. These data may include the number of tests performed, the aggregate of the numeric values calculated, the number of numeric values in each of the categories "PASS", "WARN", and "FAIL", and the amount of money input into said apparatus. These results and related data may subsequently be printed out on the printer 79, which is electrically connected to the CPU 30 by way of a conventional RS232 communications port 78. Preferably, some of the stored data is cleared from computer random access memory after being printed by the printer. In this manner, the data relates to the number of tests conducted since the last time the data in breath testing apparatus 20 were printed out, which would normally be done during a routine service call by qualified service personnel.

The routines that are processed by the CPU 30, and which are used to run the breath testing apparatus 20 of the present invention are stored in an EPROM 76, which is electrically connected to the CPU 30 by way of bus 75. The EPROM 76, 32 Kilobytes in capacity, is a standard means for storing programs for execution by a microprocessor, and various suitable forms are very well known in the art.

In the preferred embodiment, there is also provided an audio output circuit 80 electrically connected to the CPU 30, with a small speaker 82 electrically connected to the output of the audio output circuit 80. The audio output circuit 80 and the small speaker 82 are used to generate sounds, as necessary, to catch the attention of the individual user 22 or the operator of the breath testing apparatus 20, usually when there is a change in the information displayed by the alphanumeric display means 28.

A complete explanation of the method of the present invention, which method is used in the operation of the breath testing device 20 so as to sufficiently and properly guide an individual user 22 using the breath testing device 20, and thereby enable that individual user to easily use the breath testing device 20 and to understand and have confidence in the results that are ultimately presented, will now be described with reference to FIGS. 3-11. FIGS. 3-11 are standard computer programming flow charts that incorporate decision boxes in the form of a rhombus, subroutine boxes in the form of a rounded rectangle, start boxes in the form of a rounded rectangle, and message boxes in the form of a squared rectangle. Each of the boxes in FIGS. 3-11 is labelled with a three or four digit number, with either the first one or two digits as appropriate, indicating the Figure number and the last two digits indicating the box of the respective Figure. For example, in FIG. 3, the first box is labelled 300 and the last box is labelled 332, with the boxes in between labelled 302, 304, 306, . . . 328, and 330. In FIG. 10, the first box is labelled 1000 and the last box is labelled 1018, with the boxes in between labelled 1002, 1004, 1006, . . . 1014, and 1016. This numbering system has been employed for ease of reference between the text and drawings herein.

Figure 3:
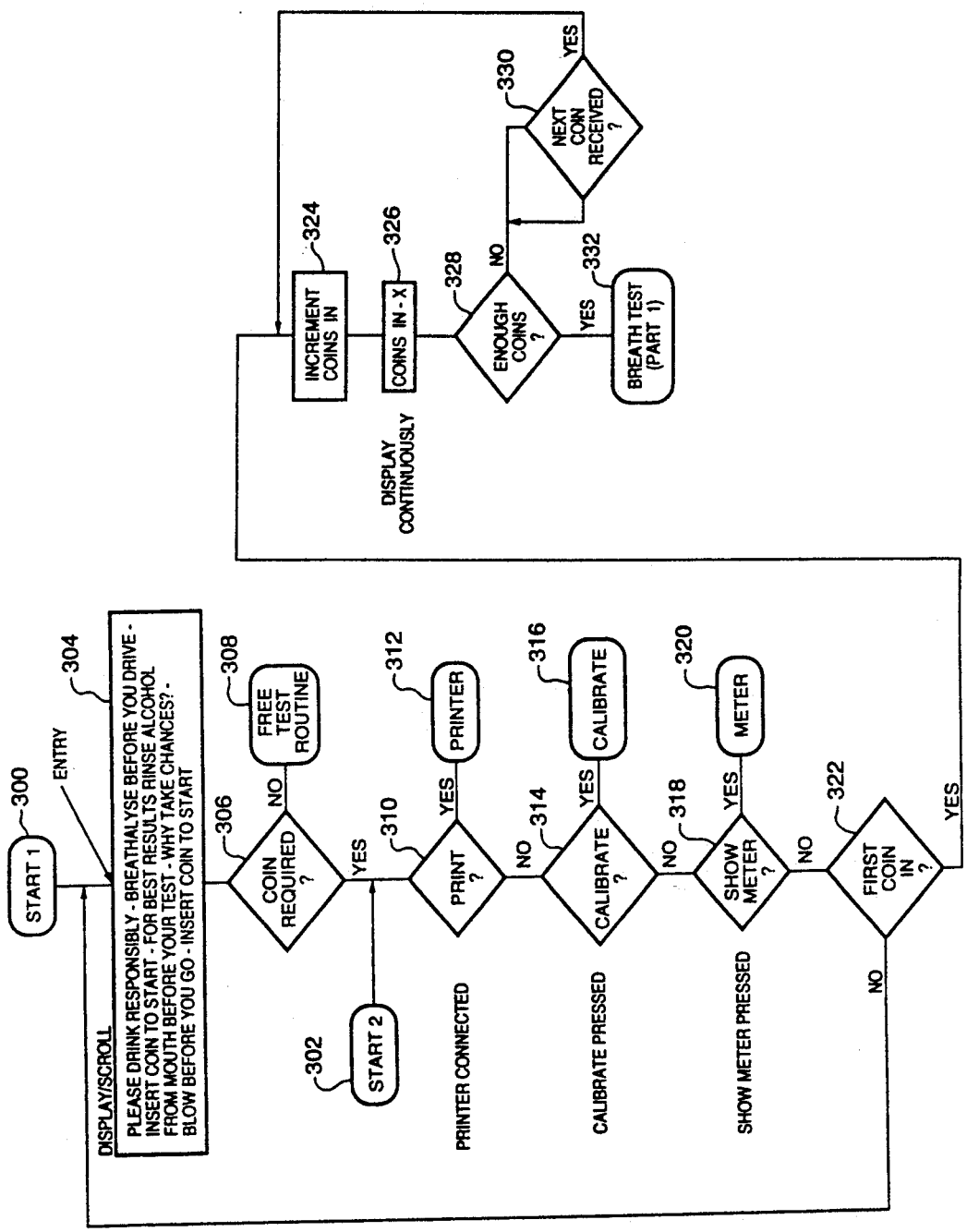
FIG. 3 is a flow chart showing the main operating routine of the method of the present invention.

Reference will now be made to FIG. 3, which shows the main operating routine, hereinafter referred to as the MAIN ROUTINE, of the method of the present invention of conducting a blood alcohol content level test on an individual user, and subsequently calculating and displaying a meaningful test result, as carried out by the device 20 just described with reference to FIGS. 3 through 11.

After electrical power to the breath testing device 20 is turned on, the method starts at box 300 which leads into an initial message being displayed by the alphanumeric display means 28, as shown in box 304, which message encourages an individual user to use the machine for safety reasons, to insert a coin to start, and also instructs the individual user 22 to rinse any alcohol from his or her mouth before preforming the test. When box 304 is reached for the first time, this message in box 304 is displayed on the alphanumeric display means 28. The entire message cannot fit at one time on to the alphanumeric display means 28 in the preferred embodiment, and thus, only the first 16 characters (letters or spaces or symbols) are displayed. On each pass through the routine between boxes 300 and 306, when box 304 is reached, the message is scrolled by one character. A small timing loop can be used, if necessary, in order to set the speed of the scrolling of the characters. In the preferred embodiment the message box 304 is "PLEASE DRINK RESPONSIBLY - BREATHALYSE BEFORE YOU DRIVE - INSERT COIN TO START - FOR BEST RESULTS RINSE ALCOHOL FROM MOUTH BEFORE YOUR TEST - WHY TAKE CHANCES? - BLOW BEFORE YOU GO - INSERT COIN TO START".

After the initial message is displayed or scrolled, the routine checks to see whether a coin is required, as shown at box 306. The routine thereby determines whether the device is in its "free test" mode, which "free test" mode is set by way of the free test option switch 71, which is located inside the breath testing device 20, and is accessible to the service operator only. In the "free test" mode, the routine diverts to the FREE TEST routine, as will be discussed in greater detail subsequently, with reference to FIG. 4. The purpose of the FREE TEST routine is to attract individual users to the breath testing device 20.

If it is determined at box 306 that coins are required, then the routine continues to box 310, where it is determined whether the printer is connected. If the printer is connected, the PRINTER routine is performed, as indicated by box 312, and as is shown in detail in FIG. 9. The PRINTER routine basically allows the information stored within the computer memory of the breath testing device 20 to be printed out by a temporarily connected printer.

If the printer is not connected, the routine continues to box 314, which determines whether the calibrate button 62 has been pressed, in which case the CALIBRATE routine is performed, as indicated by box 316 and as shown in more detail in FIG. 8. The CALIBRATE routine will be described in greater detail subsequently with reference to FIG. 8.

If the calibrate button 62 is not pressed, the routine continues to box 318, where it is determined whether the show meter button 64 is pressed. If the show meter button 64 is pressed, then the routine goes to the show meter box 320, and the routine goes to the COIN METER routine, as will be described in greater detail subsequently with reference to FIG. 11.

The routine then continues to the decision box 322 which determines whether a first coin has been entered into the coin input 52 of the breath testing device 20 and subsequently received by the coin receiving mechanism (not shown). The coin receiving mechanism is interfaced in electrically operative relation with the computer portion of the breath testing device 20 and can therefore be easily checked automatically. If there is not a coin in the coin receiving mechanism, the routine returns to box 304, where the message therein is scrolled by one character. If a first coin has been received, the routine increments (to a value of 1) in computer memory the number of coins received, as shown at box 324. This number of coins received is then displayed on the alphanumeric display means 28 in the format "COINS IN - 1", as shown at box 326. It is estimated that in some situations, such as where dollar coins are in popular use, only one coin will be necessary. In other situations, it may be necessary to have more than one coin inserted, such as four 25 cent pieces. Therefore, it is necessary to determine whether the required number of coins have been entered into the breath testing device 20. The required number of coins can be set by way of the coins required option switch 72, which is located internally in the breath testing device 20. Box 328 shows that the number of coins entered, which number is stored in computer memory, is compared with the required number of coins in order to determine whether enough coins have been entered. If not enough coins have been entered, then the routine continues to decision box 330, where it is determined whether another coin has been received. If another coin has been received, the routine returns to boxes 324, 326 and 328 subsequently to show that another coin has been entered and to again determine whether enough coins have been entered. When enough coins have been entered, the routine exits out of decision box 328 and into the subroutine box 332, which directs the routine to the BREATH TEST (part routine, which will be discussed in greater detail with reference to FIG. 5.

Figure 4:
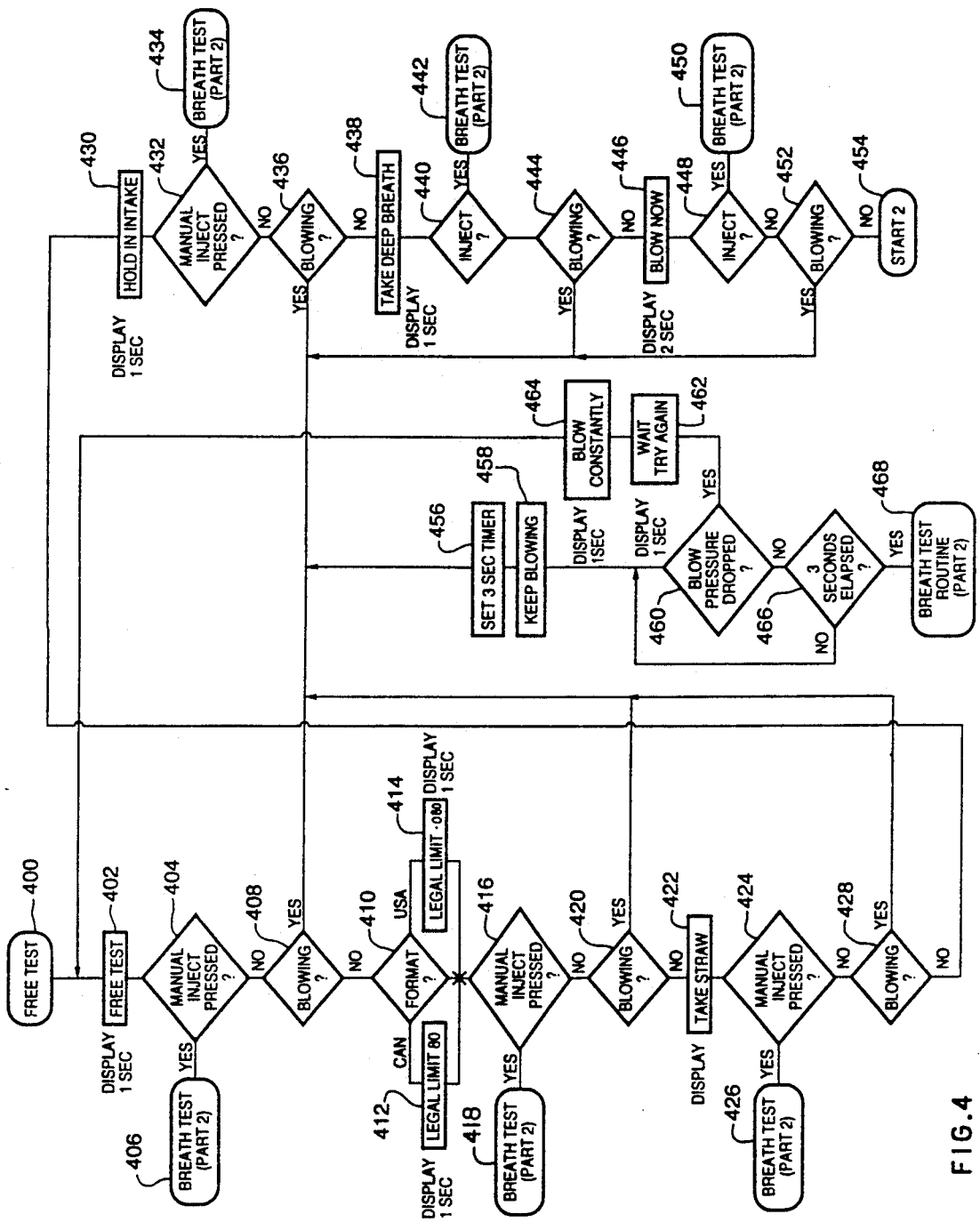
FIG. 4 is a flow chart showing the "free test routine" of the method of the present invention.

Reference will now be made to FIG. 4, which shows the FREE TEST routine, which starts at box 400. The message "FREE TEST" is displayed by the alphanumeric display means 28 for about one second, as indicated by box 402. The routine then passes to box 404, where it is determined whether the manual inject button 66 has been pressed. If the manual inject button 66 has been pressed, the routine then goes to box 406, which is a subroutine box that sends the program to the BREATH TEST (part 2) routine, which will be described in greater detail subsequently with reference to FIG. 5. If the manual inject button 66 has not been pressed, the routine continues to decision box 408 where the CPU 30 determines whether the signal being received from the pressure switch 36, which indicates whether the gauge pressure of the individual user's 22 breath sample, is at or above a threshold value gauge pressure. This threshold value gauge pressure must be realized in order to be able to assume that the individual user 22 is blowing hard enough to have the air in the bottom of his lungs blown into the breath testing device. The routine for determining whether the gauge pressure of the individual user's 22 breath sample remains at or above the threshold value for a predetermined length of time, which is necessary to ensure that the air from the bottom of the individual user's 22 lungs is expelled and therefore be available to be sampled, as will be discussed subsequently. If the individual user 22 is not blowing hard enough it is assumed that the individual user 22 is not blowing at all. The reason that the decision boxes 404 and 408 are included is to check whether the manual inject button 66 has been pressed or whether the individual user 22 is blowing at or above a threshold value gauge pressure before the individual user 22 is instructed to take a straw is because it must be considered that during a free test the individual user 22 might take a straw and commence blowing into the machine at any time. It is preferable that there is no delay, or at least a minimal delay, between the time the individual user 22 blows into the breath testing device 20 and the realization by the machine that the individual user 22 is blOWing into the machine. Groupings of boxes that are the same as, and that are joined in the same manner as, decision boxes 404 and 408 and subroutine box 406, exist throughout the FREE TEST routine. Specifically, these groupings involve boxes 424, 426 and 428, boxes 432, 434, and 436, boxes 440, 442 and 444 and boxes 448, 450 and 452. In each of these groupings, if it is determined that the manual injection button is pressed, the routine exits to the BREATH TEST routine (part 2). If it is determined that the individual user 22 is blowing at or above a threshold value gauge pressure then the routine goes to box 450, which will be described subsequently. If it is determined at any of the decision boxes 408, 420, 428, 436, 444 and 452, that the individual user 22 is not blowing at or above a threshold value gauge pressure, then the routine continues to display another message to properly instruct the individual user 22 on how to perform the test. These displayed instructions will be described in greater detail subsequently.

A message regarding the legal limit of blood alcohol content, below which a motor vehicle can be legally operated, is displayed on the alphanumeric display means 28, as shown at boxes 410 through 414. In order to do this, a format option switch 73 is sensed to determine whether the breath testing device 20 is in Canadian or U.S. format, as shown at box 410. If it is in Canadian format, the message "LEGAL LIMIT 80" (80 milligrams alcohol per 100 ml of blood) is displayed for about one second. If the format is determined to be in U.S. format, then the message "LEGAL LIMIT 0.080" (0.080 grams of alcohol in 100 ml of blood) is displayed for about one second as shown in box 414.

Again, the routine checks at box 416 to see whether the manual inject button 66 has been pressed and exits to the BREATH TEST routine (part 2) at box 418 if it has been pressed. If the manual inject button 66 has not been pressed, the routine again determines, this time at box 420, whether the individual user 22 is blowing at or above the threshold value gauge pressure, as described above. If a breath sample at or above the threshold value gauge pressure is still not being provided, thus indicating that the individual user 22 is still not blowing at all, or at least still not blowing at or above the threshold value gauge pressure, then the alphanumeric display means 28 displays a "TAKE STRAW" message, as shown in box 422.

The next instructional message to be displayed if the manual inject button 66 has not been pressed and if a breath sample has not been provided at or above the threshold value gauge pressure, is to hold the straw into the intake 26 as shown at box 430. Subsequently, box 438 shows that the next similar message instructs the individual user 22 to take a deep breath and box 446 instructs the individual user 22 to blow now. If after reaching the end of these instructional messages in boxes 402, 412 (or 414), 422, 430, 438 and 446, the individual user 22 has not blown at or above a threshold value gauge pressure, nor has the manual inject button 66 been pressed, then the routine passes to box 454, which causes the routine to exit to the beginning of the MAIN routine at box 302 on FIG. 3. The routine then is in the MAIN routine as shown in FIG. 3 until it gets to decision box 306, which again determines that no coins are required and the routine then again exits to the FREE TEST routine as shown at box 308.

If it is determined at any of boxes 408, 420, 428, 436, 444 or 452 that the individual user 22 is providing breath sample at or above a threshold value gauge pressure, then the routine goes to box 456, which indicates that a three second timer is started. An instructing message "KEEP BLOWING", as shown at box 458, is then displayed on the alphanumeric display means 28 for about one second. The gauge pressure of the individual user's 22 breath sample is again monitored to determine whether it is at or above a threshold value gauge pressure, as shown at box 460. If it has dropped below the threshold value gauge pressure, the messages "WAIT - TRY AGAIN", at box 462, and "BLOW CONSTANTLY", at box 464 are displayed, and the routine then returns to box 402 to start the FREE TEST routine over.

If it is determined at box 460 that the gauge pressure of the individual user's 22 breath sample has not dropped below the threshold value gauge pressure then the routine continues to decision box 466 to determine whether three seconds have elapsed since the three second timer was set at box 456. If three seconds have not elapsed, then the routine back to box 460 to again check the gauge pressure of the individual user's 22 breath sample. If three seconds have elapsed, the individual user 22 has been able to provide a breath sample at or above a threshold value gauge pressure for at least three seconds, and the routine exits to the BREATH TEST routine (part 2) as shown at box 468, which will be described in greater detail subsequently.

Figure 5:
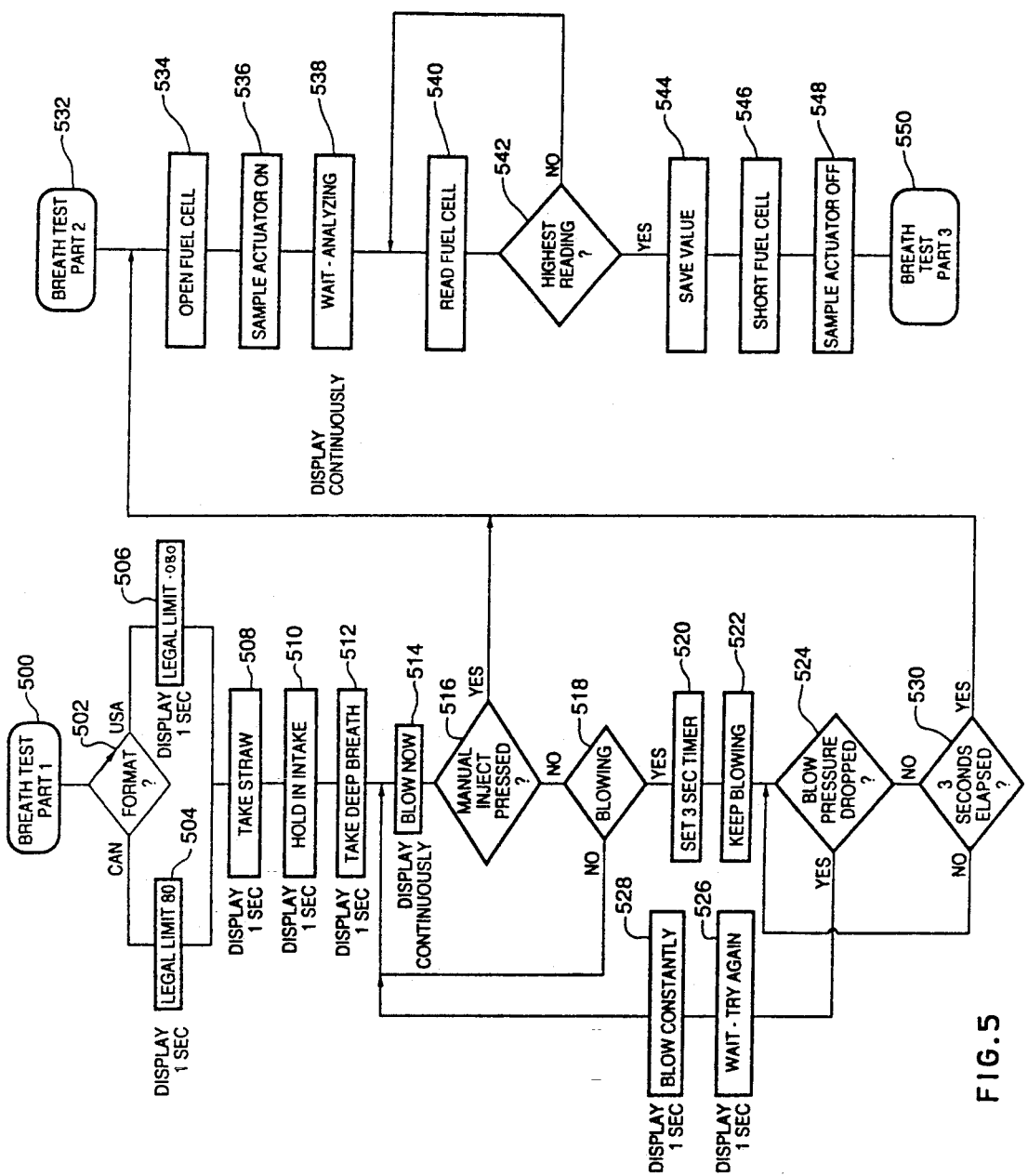
FIG. 5 is a flow chart showing the breath testing portion of the routine of the method of the present invention.

Reference will now be made to FIG. 5, which shows the BREATH TEST routine (parts 1 and 2), with the part 1 of the BREATH TEST routine starting at box 500. The BREATH TEST routine instructs the individual user 22 on the proper procedure for providing a suitable breath sample. At box 502, the appropriate format option switch 73 is checked to determine whether the device is in Canadian or U.S. format. If the device is in Canadian format, an alphanumeric message that the legal limit is 80 milligrams per 100 ml of blood is displayed for about one second, as shown at box 504, and if the device is U.S. format, an alphanumeric message that the legal limit is 0.080 is displayed for about one second as shown at box 506. The individual user 22 is then instructed as to how to initiate interfacing with the breath testing apparatus 20. Specifically, the individual user 22 is instructed to take a straw, hold the straw in the input 26, to take a deep breath, and to blow now, as shown in boxes 508, 510, 512 and 514 respectively. The messages in boxes 508, 510, and 512 are each displayed for about one second. The blow now message is displayed continuously until it is determined that the individual user 22 is blowing properly, as will be described subsequently. If the manual inject button 66 is pressed, the routine goes to the start of the BREATH TEST routine (part 2), as shown by box 532. This is because a breath sample is not required, and the sample that is manually injected is merely to be tested by the breath testing device 20.

If the manual inject button 66 is not pressed, the routine monitors the gauge pressure of the individual user's 22 breath sample in order to determine whether the gauge pressure is at or above a threshold value, as shown at box 518. If the pressure is not above the threshold value gauge pressure, then the routine returns to box 514 and again instructs the individual user 22 to blow now. If it is determined that box 518 that the gauge pressure of the individual user's 22 breath sample is at or above a threshold value gauge pressure, then it is necessary to determine whether the gauge pressure of the individual user's 22 breath sample remains at or above this threshold value gauge pressure for a predetermined length period of time, which predetermined length period of time in the preferred embodiment is three seconds. The routine continues to box 520, at which box 520 a three second timer is set. The individual user 22 is then instructed by way of an alphanumeric message to "KEEP BLOWING", as shown at box 522. This alphanumeric message in box 522 is displayed continuously until the gauge pressure of the individual user's 22 breath sample drops below the threshold value gauge pressure or until three seconds have lapsed. This can be seen at boxes 524 and 530. Box 524 is a decision box that determines whether the gauge pressure of the individual user's 22 breath sample has dropped. If the gauge pressure of the individual user's 22 breath sample has dropped, the message "WAIT TRY AGAIN", as shown in box 526 and the message "BLOW CONSTANTLY", as shown in box 528, are each displayed for about one second. The routine then returns to box 514 in order to instruct the individual user 22 to "BLOW NOW". At box 524, if the gauge pressure of the individual user's 22 breath sample has not dropped below the threshold value gauge pressure, then it is determined at box 530, whether the predetermined length period of time of three seconds has elapsed. If this predetermined length period of time of three seconds has not elapsed, the routine returns to box 524 to check again whether the gauge pressure of the individual user's 22 breath sample has dropped below the threshold value gauge pressure. If, at box 530, it is determined that three seconds have elapsed (by checking the timer that was set at box 520) then the routine advances to the BREATH TEST (part 2), as indicated at box 532.

Essentially, the routine remains within the two loops defined by boxes 514 through 528 until the individual user 22 provides a breath sample at or above the threshold value gauge pressure for three seconds or greater, or unless the manual inject button 66 is pressed.

The BREATH TEST routine (part 2), which starts at box 532, first electrically opens the alcohol concentration sensor 32 that is used to convert the captured alcohol molecules into an analog electrical signal by activating the shorting relay 41, as shown at box 534. The alcohol concentration sensor 32 is electrically closed before this point in time, by way of deactivation of the shorting relay 41' in order to ensure that it is starting from a zero voltage reference. The sample actuator is then turned on, as shown at box 536, which causes a small sample of the individual user's 22 breath to be taken immediately after the predetermined length period of time. A testing sample of the individual user's 22 breath sample then enters the alcohol concentration sensor 32, where it is reacted in a conventional manner so as to produce an analogue voltage proportional to the amount of alcohol molecules reacted.

During the time that the alcohol concentration sensor 32 is reacting, the testing sample that has been drawn from the breath sample, the alphanumeric display means 28 displays a "WAIT - ANALYSING" message, as shown at box 538, in order to inform the individual user 22 that nothing else is to be done and that he or she will have to wait for the results to be displayed. The CPU 30 then accepts a reading from the alcohol concentration sensor 32, as shown at box 540, and thereafter determines whether this is the highest reading that has been taken by comparing this reading to a previous reading. If the latest reading is the same as or lower than the previous reading, then it is determined that the previous reading is the highest reading, and this highest reading is saved in computer memory, as shown at box 544. The reading of the alcohol concentration sensor 32 and the determination whether this is the highest reading, boxes 540 and 542, are done on a continuous basis until the highest reading is achieved, as indicated by the routine path from the box 542 back to the box 540. After the highest reading value has been saved, at box 544, the alcohol concentration sensor 32 is then electrically closed by de-activation of shorting relay 41, which in actuality means that it is shorted out so that a potential voltage cannot develop across its leads, as shown at box 546. The sample actuator is then turned off, as shown at box 548, which leads to the BREATH TEST routine (part 3), as shown at box 550.

The BREATH TEST routine (part 3) will now be described in detail with reference to FIG. 6, which starts at box 600. Immediately after box 600 is decision box 602, which checks that the highest reading value saved in box 544 of FIG. 5, is less than 10 milligrams of alcohol per 100 ml of blood. If this value is less than 10, the value is reset to 0 milligrams of alcohol per 100 ml of blood as shown in box 604. The reason for this reset is that residual amounts of alcohol in the alcohol concentration sensor 32 might cause a low reading to be realized even if the individual user 22 performing the test has no alcohol in his breath sample. Displaying a non-zero result when the individual user 22 has not consumed alcohol would give the appearance that the machine is inaccurate and the individual user 22 might construe that the result, however, is not meaningful. It is acceptable, however, to have the apparatus 20 produce a zero value result when the individual user 22 has a very low blood alcohol level, below 10 milligrams of alcohol per 100 ml of blood.

Figure 6:
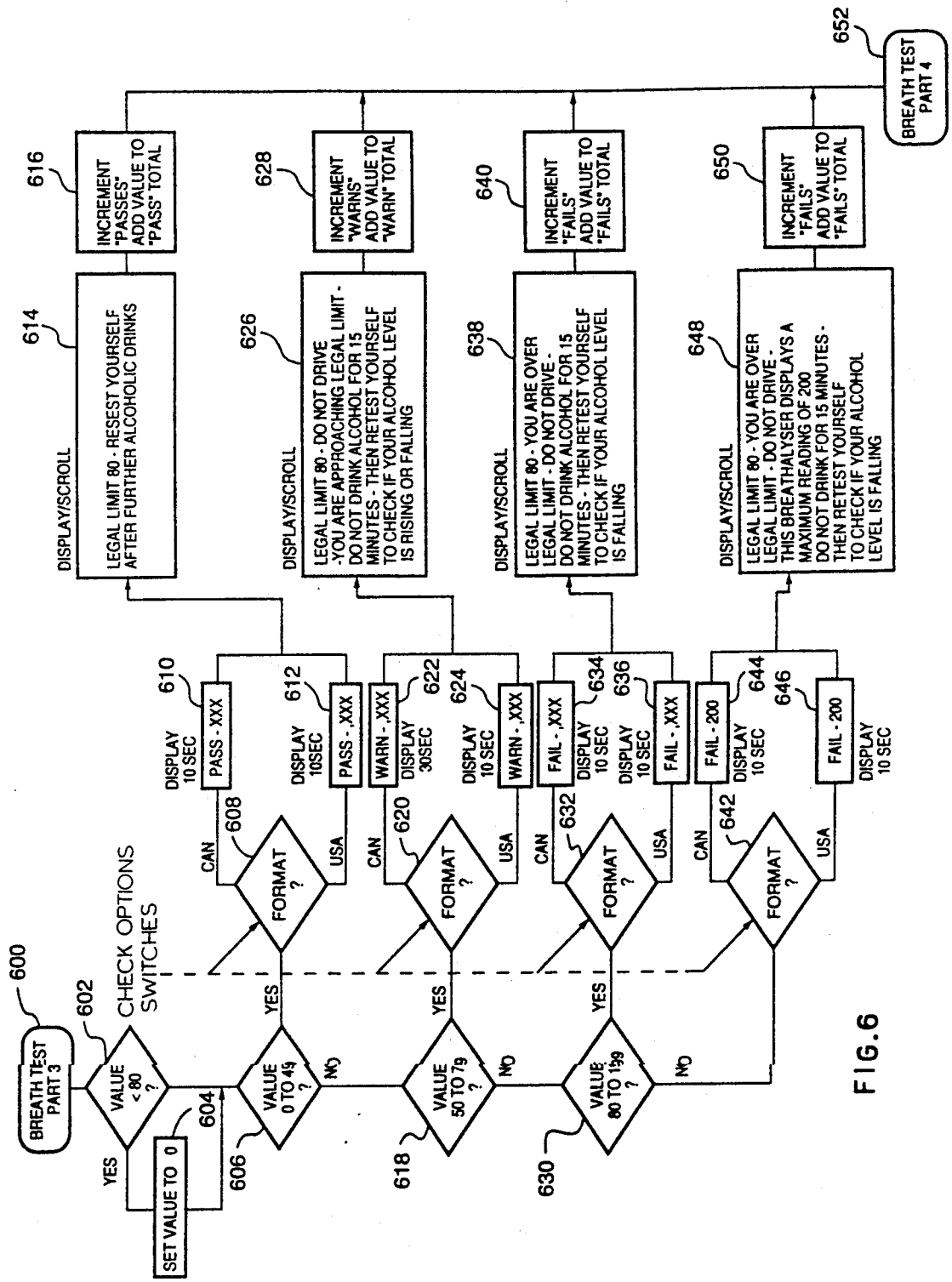
FIG. 6 is a flow chart showing a second portion of the breath testing portion of the routine of the method of the present invention.

The remaining portion of the BREATH TEST routine (part 3) as shown in FIG. 6, is merely for displaying the alphanumeric messages that allow the individual user 22 performing the test to properly understand and use the test results. The routine first passes to box 606 where it is determined whether the value is from 0 to 49, which indicates a level significantly below the legal limit. The routine passes to boxes 608, 610, and 612, which display the word "PASS" and the actual numeric result in the appropriate format, either Canadian or U.S. format, as decided at box 608, for a period of about ten seconds. The routine then passes to box 614, where the individual user 22 is reminded that the legal limit is 80, so that they may compare their score to the legal limit, and also suggests that the individual user 22 perform a retest in the event that further alcoholic drinks are consumed, preferably after a first specified length of time of fifteen minutes.

If the test value is above the range of 0 to 49, the routine passes from box 606 to box 618, which is a decision box that checks to see whether the value is between 50 and 79 inclusive. If the value is in this range, the routine passes to boxes 620, 622, and 624, which display the message "WARN" and the actual numeric result in the appropriate format, either Canadian or U.S. format, as decided at box 620, for a period of about ten seconds. The routine then passes to box 626 where the legal limit of 80 is again displayed so that the individual user 22 can compare his score with that legal limit. Further, the individual user 22 is warned not to drive as they are approaching the legal limit. The individual user 22 is also advised to not drink alcohol for a second specified length of time of fifteen minutes and then to retest himself in order to determine whether the blood alcohol content level is rising or falling. Such a determination is important because if the blood alcohol content level is rising, the individual user 22 may indeed be over the legal limit within a short period of time. This cannot be determined merely by one test. The level of 50 milligrams per liter of blood, which acts as the threshold value between a "PASS" and a "WARN" is somewhat arbitrary, but coincides with the level used by most law enforcement agencies, and which is commonly associated with an increase in accidents.

If the blood alcohol content level value is at or above 80 milligrams of alcohol per 100 ml of blood, then the routine passes to decision box 630, which decides whether the value is between 80 and 199 inclusive. If the value is within this range of 80 to 199 inclusive, then the routine passes to boxes 632, 634, and 636, which display the alphanumeric message "FAIL" and the actual numeric result in the appropriate format, either Canadian or U.S. format, as determined by decision box 632, for a period of about ten seconds. The routine then passes to box 638, where the individual user 22 is again reminded that the legal limit is 80 so that the individual user 22 can compare his level to that legal limit. The message also informs the individual user 22 that he is over the legal limit and should not drive. The message further informs the individual user 22 that a retest should be taken after a third specified length of time of fifteen minutes, without consuming alcohol in the interim.

If the level, as determined at box 630, is not within the range of 80 to 199 inclusive, then it is by process of elimination assumed that the level is at least 200 milligrams of alcohol per 100 ml of blood or higher, and a value of 200 is assumed. The routine passes to boxes 642, 644, 646, which display the alphanumeric message "FAIL" and the numeric value of 200 in the appropriate format for Canada or the U.S., depending on the determination made at decision box 642. The routine then passes to box 648 where the individual user 22 is then reminded that the legal limit is 80 milligrams of alcohol per 100 ml of blood, and that he is over the legal limit and should not drive. The individual user 22 is further informed that the maximum reading of 200 of the device has been exceeded and that a retest should be performed after a fourth specified length of time of fifteen minutes, without drinking alcohol in the interim.

The boxes 614, 626, 638, and 648, which each display lengthy explanatory messages, which explanatory messages have been detailed in the preceding paragraphs, scroll these messages across the alphanumeric display means 28, at a rate that is readable by a slightly intoxicated individual user, until the entire message has been displayed. After each of the message in boxes 614, 626, 638 and 648 have been fully displayed, the routine passes to the respective one of boxes 616, 628, 640 and 650, which causes the information regarding results of the test to be stored in computer memory. Specifically, the total number of "PASSES", "WARNINGS", and "FAILS" results are incremented as appropriate, thus allowing statistics to be retrieved from the device. Such statistics are important in verifying the usefulness of such breath testing devices in drinking establishments and the like.

It is also possible to store the actual numerical result in computer memory and subsequently retrieve a distribution of the accumulated results. Further, each time the test is performed, a counter value in the computer random access memory (RAM) 74 is incremented so that the operator of the breath testing device will know how many tests have been performed. In the preferred embodiment, the number of tests performed since the device was last serviced is stored and numbers related to this number of tests, such as money generated, money allotted to the proprietor of the drinking establishment, tax money to be forwarded to the government, and so on, can be stored in computer memory for subsequent printing out. The PRINTER routine will be described in greater detail subsequently with reference to FIG. 9.

Figure 7:
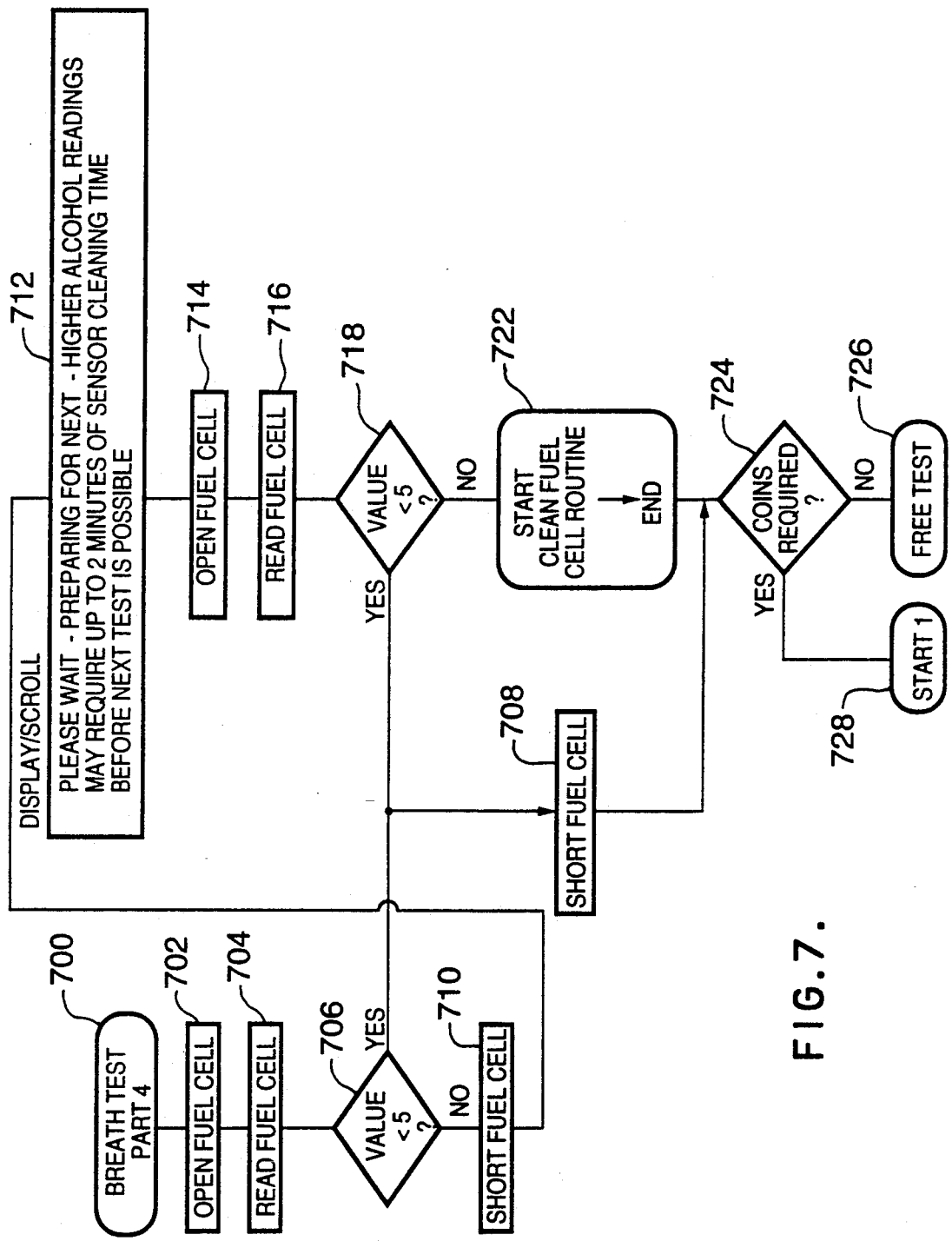
FIG. 7 is a flow chart showing the cleaning portion of the breath test routine of the method of the present invention.

Reference will now be made to FIG. 7, which shows the BREATH TEST routine (part 4) starting at box 700. The BREATH TEST routine (part 4) ensures that the alcohol concentration sensor 32 has no more than a negligible amount of residual alcohol molecules remaining in it, and is resultingly providing a zero or near zero, electrical output. The alcohol concentration sensor 32 is first electrically opened, as shown at box 702, by activating the shorting relay 41, so that the electrical output value of the alcohol concentration sensor 32 may be read at box 704. If the Value is less than 5, as determined at decision box 706, then the routine passes to box 708 where the alcohol concentration sensor 32 is electrically closed by de-activation of the shorting relay 41. Basically, this means that a value of less than 5 is considered near zero and is acceptable for performing another test. The routine then continues to box 724, which is a decision box that determines whether coins are required, in other words, whether the routine is in its FREE TEST mode or not.

If the value, as determined at decision box 706, is 5 or greater, then the alcohol concentration sensor 32 is electrically closed by de-activation of the shorting relay 41, which again causes the electrical potential generated by the alcohol concentration sensor 32 to be dissipated, at least to a small degree. A message, as shown at box 712, is then displayed that indicates that the device is preparing for a next test and cleaning the sensor and that it may require up to two minutes. This message keeps people who are waiting for the machine from thinking that the machine might be malfunctioning, since it is not available to be used during this time. Again, the alcohol concentration sensor 32 is electrically opened by activating the shorting relay 41, and read, as shown at boxes 714 and 716. Again, the reading value is determined at decision box 718. If the value is now less than 5, the routine proceeds to box 708 to electrically close the alcohol concentration sensor 32 by deactivating the shorting relay 41, as described previously. Again, the routine proceeds from box 708 as described previously.

If the value is determined to be 5 or greater at decision box 718, then the alcohol concentration sensor 32 is electrically opened by activating the shorting relay 41 before the routine subsequently proceeds to the CLEAN FUEL CELL routine, as shown at box 722. The CLEAN FUEL CELL routine will be described in greater detail subsequently with reference to FIG. 10. When the CLEAN FUEL CELL routine is finished, the routine returns to this point and then proceeds to the decision box 724 to determine whether coins are required or whether the breath testing device 20 is in its "FREE TEST" mode, as shown at box 726. The appropriate test is then proceeded with.

Reference will now be made to FIG. 8, which shows the CALIBRATE routine starting with box 800. The CALIBRATE routine is used to ensure that the breath testing device 20 is properly calibrated so as to produce accurate measurement of the blood alcohol content level in subsequent tests and is performed by a qualified and authorized service operator. For calibration purposes, an aerosol spray can (not shown) containing alcohol molecules, is used. The relative concentration of alcohol molecules that would be produced by this spray can has previously been tested in a factory setting and this value is indicated on the can. The breath testing device 20 must be calibrated so as to indicate this number in the following manner. The alphanumeric display means 28 prompts the operator to inject the sample of the gas and alcohol molecules from the aerosol spray can at box 804. The service operator then sprays a sample into the input 26 and then presses the manual inject button 66 so that the sample is taken immediately without the necessity of a threshold value gauge pressure to be realized. The alcohol concentration sensor 32 is then electrically opened by activation of the shorting relay 41 so that a potential voltage corresponding to the concentration of alcohol molecules received by the alcohol concentration sensor 32 can be produced at its electrical leads, as shown at box 808. The sample actuator is turned on, as shown as box 810, and a sample is captured into the alcohol concentration sensor 32 as shown at box 812. This reading is amplified and input into the peak detector circuit 44, and the peak reading that is realized is passed to the CPU 30 through the analogue-to-digital converter 46, and then is displayed on the alphanumeric display means 28 as shown by box 814. This peak reading is then stored in the computer random access memory (RAM) 74. A small waiting loop is set up at box 816, where the routine waits for the value to be received from the peak detector circuit 44 and converted to a digital that can be used. Once the determination has been made at box 816 that the highest reading is available, then the routine continues to box 818, which causes the reading to be held in computer random access memory 74.

The routine then proceeds to decision box 820, which determines whether a period of ten seconds has elapsed. Basically, this is for timing purposes in order to allow the service operator performing the CALIBRATION routine a time of ten seconds in which to finish the calibration of the breath testing device 20. During the ten second period, the loop in the routine defined by the boxes 820, 822, 824, and 826 and the loop that goes from box 826 back to box 820 repeatedly causes the held value of the alcohol concentration sensor 32, which was stored in random access computer memory 74 at box 818, to be read and the measured level of the blood alcohol content to be displayed. As indicated at box 826, the calibrate control, in the form of potentiometer 42, must be adjusted until the reading shown in box 824 matches the calibration number on the aerosol spray can. Once the ten second period has elapsed, as determined at decision box 820, the routine passes to box 828 which turns the sample actuator off, and then passes to box 830 wherein the alcohol concentration sensor 32 is electrically closed by de-activation of shorting relay 41. The alcohol concentration sensor 32 is then cleaned by way of the CLEAN FUEL CELL routine, as shown at box 834, in order to purge any residual alcohol molecules from the alcohol concentration sensor 32. The CALIBRATION routine is then ended, as shown at box 836.

Figure 9:
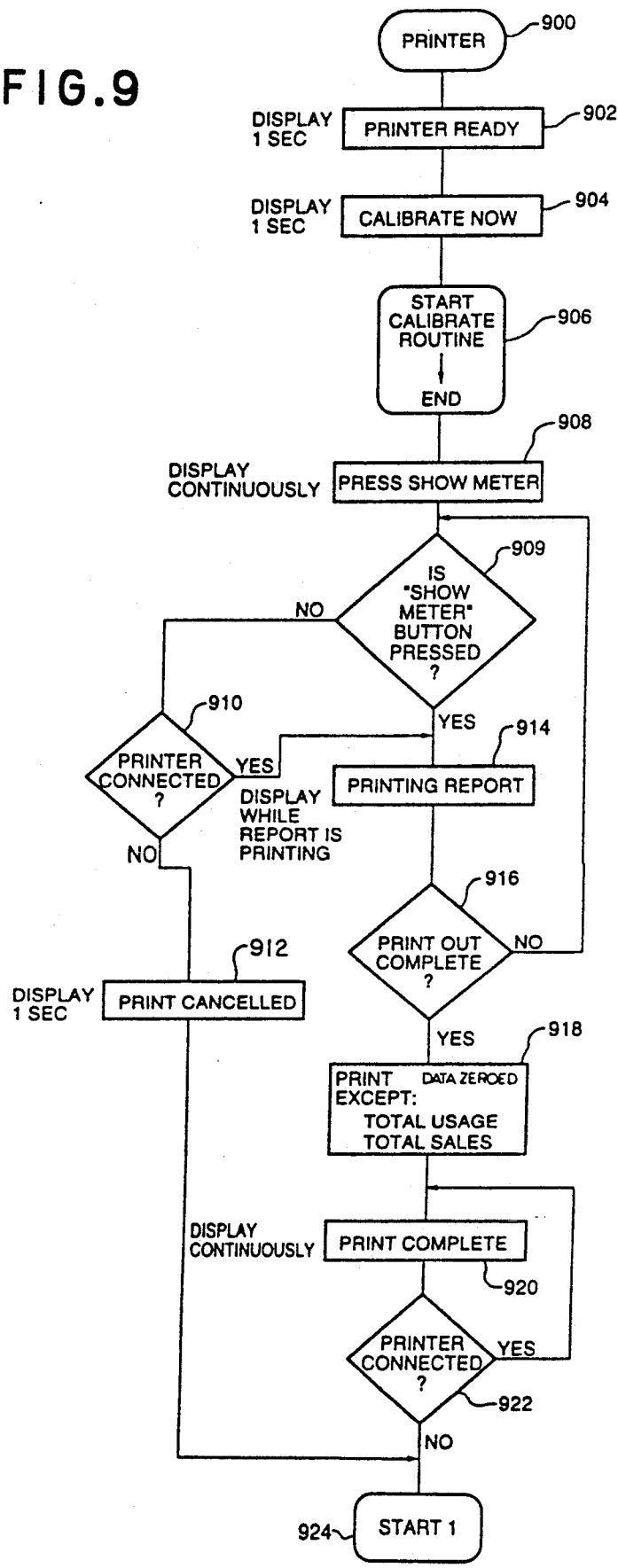
FIG. 9 is a flow chart showing the printer routine of the method of the present invention.
Figure 10:
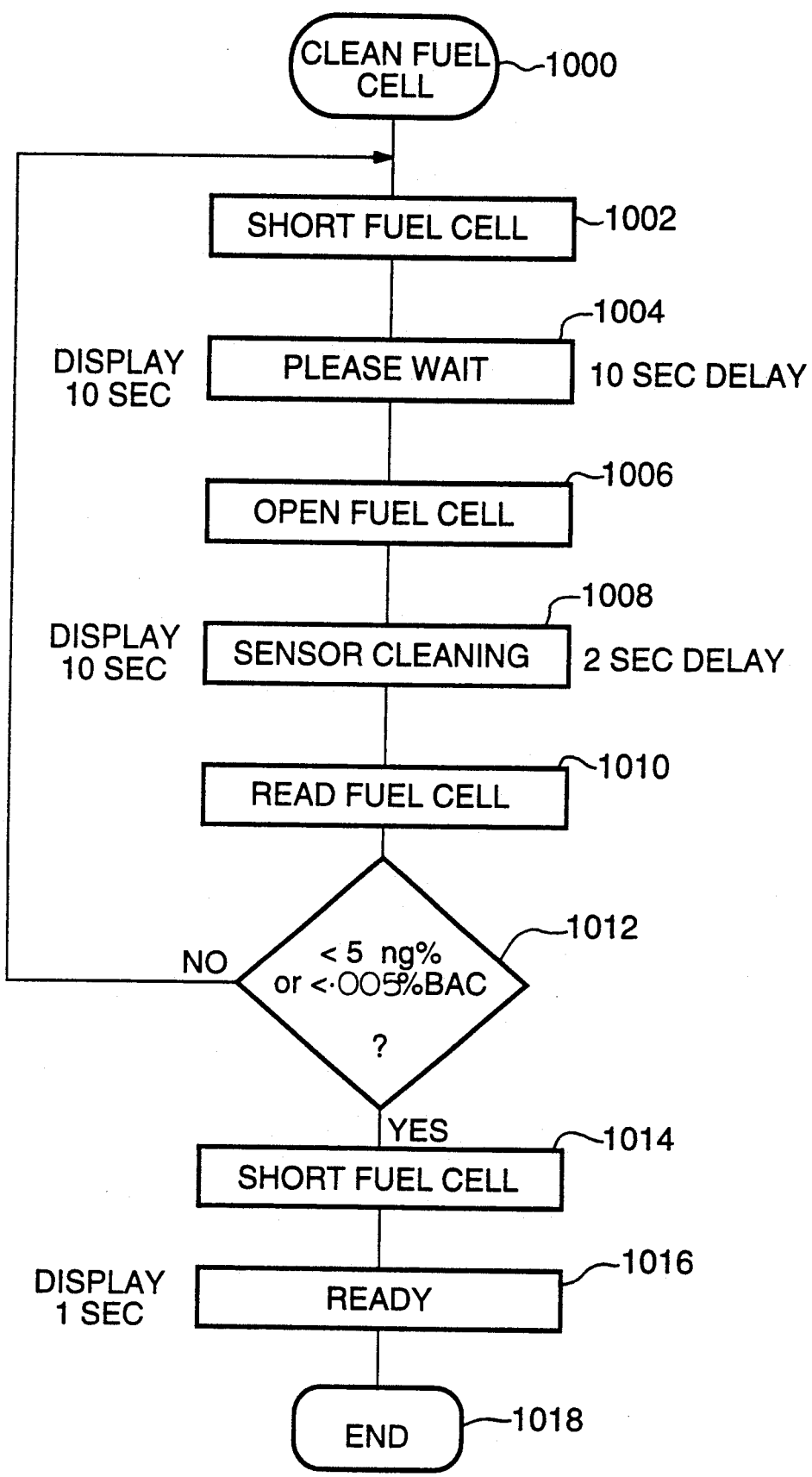
FIG. 10 is a flow chart showing the fuel cell cleaning routine of the method of the present invention.

Reference will now be made to FIG. 9, which shows the PRINTER routine, starting at box 900. The PRINTER routine is invoked by way of the printer 79 being electrically connected to the RS232 communications port 78. The alphanumeric display means 28 displays a message that the printer 79 is ready, as shown at box 902, for a period of about one second and then displays an instruction to calibrate the device now, as shown at box 904, for a period of about one second. The routine then jumps to the CALIBRATE routine, as shown at box 906 and returns to instruct the service operator to press the show meter button 64, as shown at box 908 and then progresses to decision box 909, where it is determined whether the show meter button 64 has been pressed. If the show meter button 64 has been pressed, the routine proceeds to print out the report, as shown at box 914, which displays a "PRINTING REPORT" message on the alphanumeric display means 28. If the "SHOW METER" button has not been depressed, the routine proceeds to decision box 910 where it is determined whether a printer is connected. If there is no printer connected then a "PRINT CANCELLED" message is displayed for about one second, as shown at box 912, and the routine then proceeds to the end of the PRINTER routine where it jumps to the start of the main routine, which is box 300 in FIG. 3, as shown in box 924. If the printer is connected by the determination at box 910, then the alphanumeric display means 28 displays that a report is printing, as shown by box 914, and the information stored in computer memory is printed out by the connected printer, one character at a time. After printing each character the routine determines whether the print-out is complete by detecting a null value at the end of the print-out string of information, as shown at box 916. If the print-out is not complete the routine returns to decision box 909. If the print-out is complete, the routine continues to box 918, which shows that the data that have been stored in computer random access memory (RAM) 74, such as the number of tests that have been performed since the last servicing and print-out and the number of each test that have fallen into each of the categories "PASS", "WARN" and "FAIL" are then set to zero. The routine then circulates in a small loop as defined as boxes 920, 922 and the arrow going from box 922 to box 920 while waiting for the printer to be disconnected. At box 920 "PRINT COMPLETE" message is displayed on the alphanumeric display means 28. At box 922, it is determined whether the printer 79 is connected. If the printer 79 is still connected then the routine goes to box 920 to continue to display the "PRINT COMPLETE" message. Once the printer 79 is disconnected, the routine falls through the decision box 922 and passes to the end of the PRINTER routine where it returns to the start of the MAIN routine at box 300, as indicated by box 924.

The CLEAN FUEL CELL routine will now be described with reference to FIG. 10, which starts at box 1000. The alcohol concentration sensor 32 is first electrically closed by deactivating shorting relay 41, as shown at box 1002. A "PLEASE WAIT" message is displayed on the alphanumeric display means 28 for a period of about ten seconds in order to allow all of the electrochemical potential of the alcohol concentration sensor 32 to be exhausted. The alcohol concentration sensor 32 is then electrically opened by activation of shorting relay 41 in order that the electrical potential of the alcohol concentration sensor 32 can be read, as shown at box 1006. Another message is displayed, as shown at box 1008, that indicates the alcohol concentration sensor 32 is being cleaned. The value of the electrical potential of the alcohol concentration sensor 32 is then read, as shown at box 1010. The determination is made whether this reading is less than 5 milligrams of alcohol per 100 ml of blood at decision box 1012, if it is not less than 5, the routine returns to box 1002 to perform the cleaning operation again. If it is determined at box 1012 that the reading from the alcohol concentration sensor 32 is less than 5 milligrams per 100 ml then the alcohol concentration sensor 32 is electrically closed by de-activation of the shorting relay 41 so as to not build up any electrical potential, as indicated at box 1014. A "READY" message is then displayed for about one second, as indicated by box 1016, and the end of the CLEAN FUEL CELL routine is then reached, as indicated at box 1018.

Figure 11:
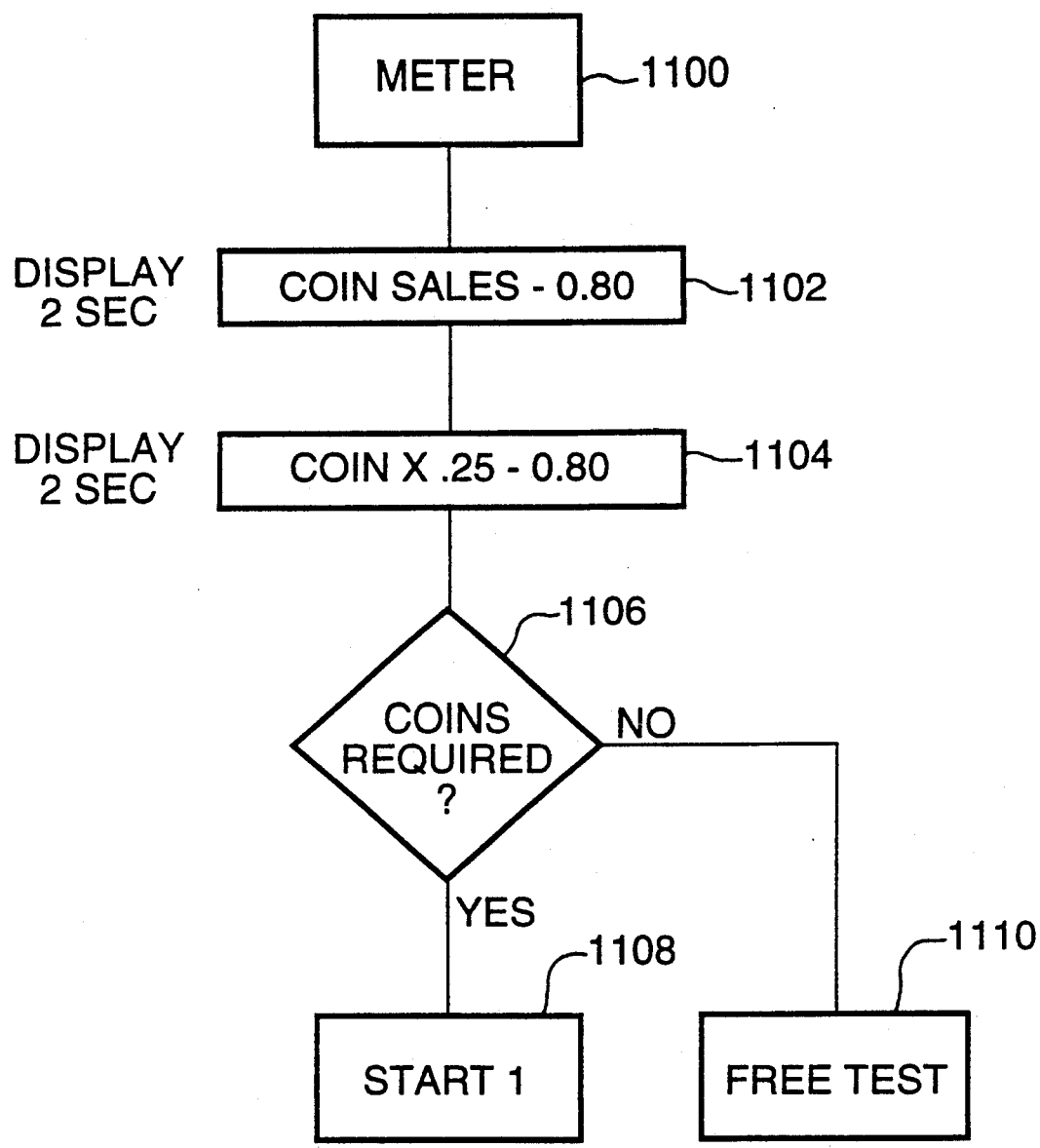
FIG. 11 is a flow chart showing the coin meter routine of the method of the present invention.

Reference will now be made to FIG. 11 in order to describe the COIN METER routine, starting a box 1100. The COIN METER routine displays the number of sales that have been made and the commission for the owner of the establishment as shown at boxes 1102 and 1104. A determination is then made a decision box 1106 whether coins are required. If it is determined that coins are not required then the routine jumps to the FREE TEST routine, as indicated by box 1110. If it is determined that coins are required, then the routine jumps to the start of the routine at box 300, as indicated by box 1108.

The overall operation of the breath testing apparatus 20 by the individual user 22 will now be described. The individual user 22 stands in front of the breath testing apparatus 20 and reads the message, as shown in box 304 of FIG. 3. This message in part prompts the individual user 22 to insert a coin to start the breath testing apparatus 20 so that a test may be performed. The individual user 22 then inserts one or more coins, as required, which coins are counted by the portion of the routine represented by boxes 322-332, as shown in FIG. 3. Once the required number of coins have been inserted, the alphanumeric display means 28 prompts the individual user 22 to "TAKE A STRAW", to "HOLD IN INTAKE", to "TAKE DEEP BREATH", and to "BLOW NOW". The "BLOW NOW" message is displayed continuously until the individual user 22 is blowing at or above a threshold value gauge pressure. If this threshold value gauge pressure is not maintained for three seconds, the messageS "WAIT - TRY AGAIN" and "BLOW CONSTANTLY" are each displayed on the alphanumeric display means 28 for a period of one second. The message "BLOW NOW" is thereafter again displayed continuously on the alphanumeric display means 28. If the blow pressure remains at or above the threshold value gauge pressure for a period of three seconds, the actual test is then proceeded with. A signal from the CPU 30 causes the solenoid 38 to release the set button 35 on the metering valve 34 to thereby allow a testing sample to be drawn from the feed tube 27 into the alcohol concentration sensor 32. The analogue voltage from the output 33 of the alcohol concentration sensor 32 is fed through the operational amplifier 40, and into the peak detector circuit 44. As the alcohol molecules are reacted by the alcohol concentration sensor 32 the signal reaching the peak detector circuit 44 increases correspondingly. When the signal reaching the peak detector circuit 44 reaches a maximum, a corresponding voltage is sent to the analogue to digital converter 46. The converted digital value from the analogue to digital converter 46 is fed into the CPU 30, which takes this value and compares it to numeric standards, which have been previously stored within the EPROM 76. These predetermined values are typically 50, which represents 50 milligrams per 100 ml of blood, and is typically considered a threshold between the categories "PASS" and "WARN", and 80, which represents 80 milligrams per 100 ml of blood and is the value that is typically used by law to determine whether a person is above the legal limit for operating a motor vehicle. The actual numeric value as determined by the breath testing apparatus 20 operating according to the routine described herein is then displayed on the alphanumeric display means 28 along with the category of "PASS", "WARN", or "FAIL". These results are displayed for a period of ten seconds, after which, related messages, as shown in FIG. 6, at boxes 614, 616, 626, 628, 638, 640, 648, and 650, are displayed on the alphanumeric display means 28. The breath testing apparatus 20 then cleans the alcohol concentration sensor 32 before it ends that particular test sequence and returns to its initial waiting stage, where the original prompting message, as shown in box 304, is again displayed while the breath testing apparatus 20 waits for another individual user to insert coins and perform the test.

We claim:

1. An automated unsupervised apparatus for conducting a blood alcohol content level test on an individual user, and subsequently discerning and displaying a meaningful test result, said apparatus comprising:

alphanumeric display means for instructing said individual user to commence blowing into said apparatus so as to provide a breath sample;

pressure switch means for monitoring the gauge pressure of said individual user's breath sample in order to determine whether said gauge pressure is at or above a threshold value gauge pressure;

timer means for determining whether said gauge pressure of said individual user's breath sample remains at or above said threshold value gauge pressure for a predetermined length of time;

wherein, said alphanumeric display means also instructs said individual user to wait and blow again in the event that said gauge pressure does not remain at or above said threshold value for said predetermined length of time;

means for capturing a testing sample that is a representative portion of said individual user's breath sample subsequent to said individual user providing a breath sample at or above said threshold value for said predetermined length of time;

means for effecting an automated electrochemical analysis of said testing sample;

means for producing a measurement value of the alcohol content of said testing sample; and, microprocessor means for calculating a numeric value derived from said measurement value, said numeric value thereby being related to said individual user's blood alcohol content level;

wherein, said alphanumeric display means also displays to said individual user one of either (1) the category corresponding to said numeric value as being one of "pass", "warn", and "fail" and (2) said numeric value derived from said measurement value.

2. The apparatus of claim 1, wherein said alphanumeric display means is a sixteen character display.

3. The apparatus of claim 1, wherein said timer means is a routine operating within said microprocessor.

4. The apparatus of claim 1, wherein said means for effecting an automated electrochemical analysis of said breath sample comprises an alcohol concentration sensor.

5. The apparatus of claim 4, wherein said means for effecting an automated electrochemical analysis of said breath sample further comprises an operational amplifier, a peak circuit detector and an analogue to digital convertor.

6. The apparatus of claim 4, wherein said alcohol concentration sensor is a fuel cell.

7. The apparatus of claim 1, wherein said means for capturing a testing sample that is a representative portion of said individual user's breath sample comprises a metering valve operating in conjunction with said alcohol concentration sensor.

8. The apparatus of claim 1, further comprising computer random access memory for storing data related to said calculated numeric values.

9. The apparatus of claim 8, further comprising a printer electrically connected to said microprocessor, said printer for printing out said data stored in said computer random access memory.

10. An automated method of conducting a blood alcohol content level test on an individual user through the use of an unsupervised apparatus, and subsequently discerning and displaying a meaningful test result, said method comprising the steps of:

(a) (i) instructing said individual user by way of an alphanumeric display means to commence blowing into said apparatus so as to provide a breath sample;

(b) monitoring the gauge pressure of said individual user's breath sample in order to determine whether said gauge pressure is at or above a threshold value gauge pressure;

(c) determining whether said gauge pressure of said individual user's breath sample remains at or above said threshold value gauge pressure for a predetermined length of time;

(d) instructing said individual user by way of said alphanumeric display means to wait and blow again in the event that said gauge pressure does not remain at or above said threshold value for said predetermined length of time;

(e) performing steps (c) and (d) until said individual user provides a breath sample at or above said threshold value for said predetermined length of time;

(f) capturing a testing sample that is a representative portion of said individual user's breath sample subsequent to said individual user providing a breath sample at or above said threshold value for said predetermined length of time;

(g) effecting an automated electrochemical analysis of said breath sample so as to produce a measurement value of the alcohol content of said representative portion of said individual user's breath sample;

(h) obtaining said measurement value resulting from said automated electrochemical analysis;

(i) calculating a numeric value derived from said measurement value, said numeric value thereby being related to said individual user's blood alcohol content level; and, (j) (i) displaying to said individual user by way of said alphanumeric display means, one of either: (1) the category corresponding to said numeric value as being one of "pass", "warn", and "fail"; and, (2) said numeric value derived from said measurement value.

11. The method of claim 10, further comprising the step of:

(j) (ii) displaying to said individual user by way of said alphanumeric display means the other one of: (1) the category corresponding to said numeric value as being one of "pass", "warn", and "fail"; and, (2) said numeric value derived from said measurement value.

12. The method of claim 11, wherein step (a) further comprises the step of:

instructing said individual user by way of said alphanumeric display means as to how to initiate interfacing with the apparatus in order to commence the subsequent testing sequence.

13. The method of claim 11, wherein the first step of said method comprises the step of:

informing said individual user by way of said alphanumeric display means of the legal limits of a driver's blood alcohol content level.

14. The method of claim 13, further comprising the step of:

(k) where:
  (i) said category is "pass":
    (a) displaying to said individual user by way of said alphanumeric display means a message to encourage said individual user to perform a retest after a first specified length of time in the event that said individual user consumes additional alcohol;
  (ii) said category is "warn":

(a) displaying to said individual user by way of said alphanumeric display means a message to encourage said individual user to perform a retest after a second specified length of time without consuming alcohol in the interim;

(iii) said category is "fail":

(a) displaying to said individual user by way of said alphanumeric display means a message to encourage said individual user to perform a retest after a third specified length of time without consuming alcohol in the interim.

15. The method of claim 14, further comprising the step of:

(k) where:

(ii) said category is "warn":

(b) informing said individual user by way of said alphanumeric display means to determine whether his blood alcohol content level is rising or falling;

(c) cautioning said individual user not to drive in the event that blood alcohol content level appears to be rising;

(iii) said category is "fail":

(b) informing said individual user by way of said alphanumeric display means to determine whether his blood alcohol content level is rising or falling;

(c) cautioning said individual user not to drive.

16. The method of claim 15, further comprising the step of:

instructing said individual user by way of said alphanumeric display means to stop blowing when said individual user provides a breath sample having a gauge pressure at or above said threshold value for said predetermined length of time.

17. The method of claim 16, further comprising the step of:

instructing said individual user by way of said alphanumeric display means to first take a deep breath before blowing.

18. The method of claim 16, further comprising the step of:

(a) (ii) displaying an alphanumeric message for instructing said individual user to continue blowing when said gauge pressure reaches a threshold value.

19. The method of claim 18, further comprising the step of:

(k) where:

(iv) said category is "fail" and said blood alcohol level is above an extremely elevated level:

(a) informing said individual user by way of said alphanumeric display means that his blood alcohol content is above said elevated level and cannot be properly determined;

(b) displaying to said individual user by way of said alphanumeric display means a message to encourage said individual user to perform a retest after a fourth specified length of time without consuming alcohol in the interim;

(c) cautioning said individual user not to drive.

20. The method of claim 19, wherein said extremely elevated level is 200 milligrams of alcohol per 100 ml of blood.

21. The method of claim 14, wherein said first specified length of time is about fifteen minutes.

22. The method of claim 14, wherein said second specified length of time is about fifteen minutes.

23. The method of claim 14, wherein said third specified length of time is about fifteen minutes.

24. The method of claim 14, wherein said fourth specified length of time is about fifteen minutes.

25. The method of claim 10, further comprising the step of:

displaying an alphanumeric message for instructing said individual user to blow constantly when said individual user has blown above said threshold value of said gauge pressure for a length of time less than said predetermined length of time.

26. The method of claim 10, further comprising the step of:

storing data in computer random access memory, said data related to said calculated numeric values.

27. The method of claim 26, wherein said data include the number of tests performed, the aggregate of the numeric values calculated, the number of numeric values in each of the categories "PASS", "WARN", and "FAIL", and the amount of money input into said apparatus.

28. The method of claim 26, further comprising the step of:

printing said stored data by way of a printer.

29. The method of claim 28, further comprising the step of:

clearing at least some of the stored data after said stored data are printed.

* * * * *